US011878151B2

(12) United States Patent
Saint et al.

(10) Patent No.: US 11,878,151 B2
(45) Date of Patent: Jan. 23, 2024

(54) INTELLIGENT MEDICATION DELIVERY SYSTEMS AND METHODS FOR DOSE SETTING AND DISPENSING MONITORING

(71) Applicant: Medtronic MiniMed, Inc., Northridge, CA (US)

(72) Inventors: Sean Saint, San Diego, CA (US); Jack Pryor, Ladera Ranch, CA (US); Arnold Holmquist, Dana Point, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 41 days.

(21) Appl. No.: 17/846,406

(22) Filed: Jun. 22, 2022

(65) Prior Publication Data

US 2022/0347390 A1      Nov. 3, 2022

Related U.S. Application Data

(63) Continuation of application No. 17/156,681, filed on Jan. 25, 2021, now Pat. No. 11,369,743, which is a
(Continued)

(51) Int. Cl.
*G08B 27/00* (2006.01)
*A61M 5/315* (2006.01)
(Continued)

(52) U.S. Cl.
CPC .......... *A61M 5/3155* (2013.01); *G08B 21/02* (2013.01); *G08B 21/182* (2013.01);
(Continued)

(58) Field of Classification Search
CPC .......... A61M 5/3155; A61M 2230/201; A61M 2205/502; A61M 2205/3317;
(Continued)

(56) References Cited

U.S. PATENT DOCUMENTS

| 4,498,904 A | 2/1985 | Turner et al. |
| 4,515,584 A | 5/1985 | Abe et al. |

(Continued)

FOREIGN PATENT DOCUMENTS

| EP | 0298067 A1 | 1/1989 |
| EP | 0513128 A1 | 11/1992 |

(Continued)

OTHER PUBLICATIONS

Cision PR News Wire, "CompaNion Medical Announces Insights by InPen, the Future of MDI Reports", Jun. 20, 2018.
(Continued)

*Primary Examiner* — Tanmay K Shah
(74) *Attorney, Agent, or Firm* — Carter, DeLuca & Farrell LLP

(57) ABSTRACT

Systems, devices, and techniques are disclosed for administering and tracking medicine to patients and providing health management capabilities for patients and caregivers. In some aspects, an intelligent medicine administering system includes a medicine injection device having a multi-channel encoder that detects fault conditions (e.g., such as open or short circuits) and a patient user's companion device including a software application operable to implement algorithms for detecting faults and communication loss and alerting the patient user for safety and fail-safes of the medicine injection device.

20 Claims, 17 Drawing Sheets

Related U.S. Application Data continuation of application No. 16/407,046, filed on May 8, 2019, now Pat. No. 10,898,653.

(60) Provisional application No. 62/668,723, filed on May 8, 2018.

(51) Int. Cl.
*G08B 21/18* (2006.01)
*G08B 21/02* (2006.01)
*A61K 38/28* (2006.01)

(52) U.S. Cl.
CPC ............ *G08B 21/185* (2013.01); *A61K 38/28* (2013.01); *A61M 2205/18* (2013.01); *A61M 2205/3317* (2013.01); *A61M 2205/3584* (2013.01); *A61M 2205/3592* (2013.01); *A61M 2205/50* (2013.01); *A61M 2205/502* (2013.01); *A61M 2205/52* (2013.01); *A61M 2230/201* (2013.01); *A61M 2230/63* (2013.01)

(58) Field of Classification Search
CPC .......... A61M 2205/52; A61M 2205/18; A61M 2205/3584; A61M 2205/50; A61M 2205/3592; A61M 2230/63; G08B 21/185; G08B 21/182; G08B 21/02; A61K 38/28
USPC .................................................... 340/539.11
See application file for complete search history.

(56) References Cited

U.S. PATENT DOCUMENTS

| | | |
|---|---|---|
| 4,950,216 A | 8/1990 | Weder |
| 4,973,318 A | 11/1990 | Holm et al. |
| 4,988,660 A | 1/1991 | Campbell |
| 5,279,586 A | 1/1994 | Balkwill |
| 5,626,566 A | 5/1997 | Petersen et al. |
| 5,681,285 A | 10/1997 | Ford et al. |
| 5,822,715 A | 10/1998 | Worthington et al. |
| 5,925,021 A | 7/1999 | Castellano et al. |
| 5,984,900 A | 11/1999 | Mikkelsen |
| 6,004,297 A | 12/1999 | Steenfeldt-Jensen et al. |
| 6,042,571 A | 3/2000 | Hjertman et al. |
| 6,235,004 B1 | 5/2001 | Steenfeldt-Jensen et al. |
| 6,302,855 B1 | 10/2001 | Lav et al. |
| 6,482,185 B1 | 11/2002 | Hartmann |
| 6,817,986 B2 | 11/2004 | Slate et al. |
| 7,591,801 B2 | 9/2009 | Brauker et al. |
| 7,905,833 B2 | 3/2011 | Brister et al. |
| 7,955,303 B2 | 6/2011 | Burren et al. |
| 7,976,492 B2 | 7/2011 | Brauker et al. |
| 8,221,356 B2 | 7/2012 | Enggaard et al. |
| 8,229,535 B2 | 7/2012 | Mensinger et al. |
| 8,231,531 B2 | 7/2012 | Brister et al. |
| RE43,834 E | 11/2012 | Steenfeldt-Jensen et al. |
| 8,460,231 B2 | 6/2013 | Brauker et al. |
| 8,565,848 B2 | 10/2013 | Brister et al. |
| D694,252 S | 11/2013 | Helm |
| 8,591,455 B2 | 11/2013 | Mensinger et al. |
| 8,663,109 B2 | 3/2014 | Brister et al. |
| 8,721,585 B2 | 5/2014 | Mensinger et al. |
| 8,750,955 B2 | 6/2014 | Mensinger et al. |
| 8,808,228 B2 | 8/2014 | Brister et al. |
| 8,882,741 B2 | 11/2014 | Brauker et al. |
| 8,920,401 B2 | 12/2014 | Brauker et al. |
| 8,926,585 B2 | 1/2015 | Brauker et al. |
| D727,928 S | 4/2015 | Allison et al. |
| 9,020,572 B2 | 4/2015 | Mensinger et al. |
| 9,050,413 B2 | 6/2015 | Brauker et al. |
| D738,385 S | 9/2015 | Lim et al. |
| 9,143,569 B2 | 9/2015 | Mensinger et al. |
| 9,155,843 B2 | 10/2015 | Brauker et al. |
| D747,333 S | 1/2016 | Supino et al. |
| D748,101 S | 1/2016 | Bang et al. |
| D748,126 S | 1/2016 | Sarukkai et al. |
| D749,103 S | 2/2016 | Song |
| D753,685 S | 4/2016 | Zimmerman et al. |
| D754,689 S | 4/2016 | Lee |
| D759,684 S | 6/2016 | Bijlani et al. |
| D761,280 S | 7/2016 | Chung et al. |
| D763,308 S | 8/2016 | Wang et al. |
| D766,958 S | 9/2016 | Salazar Cardozo et al. |
| 9,446,194 B2 | 9/2016 | Kamath et al. |
| D777,760 S | 1/2017 | Zhao et al. |
| D781,890 S | 3/2017 | Gathman et al. |
| D783,037 S | 4/2017 | Hariharan et al. |
| D783,648 S | 4/2017 | Vazquez et al. |
| D784,391 S | 4/2017 | Yuguchi et al. |
| D785,025 S | 4/2017 | Zimmerman et al. |
| D786,273 S | 5/2017 | Herman et al. |
| 9,672,328 B2 | 6/2017 | Saint et al. |
| D791,806 S | 7/2017 | Brewington et al. |
| D794,047 S | 8/2017 | Gandhi et al. |
| D795,900 S | 8/2017 | Bischoff et al. |
| D795,919 S | 8/2017 | Bischoff et al. |
| D795,927 S | 8/2017 | Bischoff et al. |
| D797,760 S | 9/2017 | Tsujimura et al. |
| D798,312 S | 9/2017 | Tsujimura et al. |
| 9,775,543 B2 | 10/2017 | Brister et al. |
| D808,986 S | 1/2018 | Dudey |
| D809,544 S | 2/2018 | Ambielli |
| D809,545 S | 2/2018 | Ban et al. |
| D811,425 S | 2/2018 | Olsen et al. |
| D815,127 S | 4/2018 | Phillips et al. |
| D815,667 S | 4/2018 | Yeung |
| 9,937,293 B2 | 4/2018 | Brauker et al. |
| D819,043 S | 5/2018 | Yamaura et al. |
| D820,297 S | 6/2018 | Gardner et al. |
| 9,996,668 B2 | 6/2018 | Reihman et al. |
| D831,049 S | 10/2018 | Agarwal et al. |
| D831,684 S | 10/2018 | Ghosh |
| D832,292 S | 10/2018 | Hu et al. |
| D832,870 S | 11/2018 | Hu |
| D833,469 S | 11/2018 | Coleman et al. |
| D835,118 S | 12/2018 | Lee et al. |
| D837,807 S | 1/2019 | Baber et al. |
| D838,734 S | 1/2019 | Kruse et al. |
| 10,169,539 B2 | 1/2019 | Reihman et al. |
| D842,888 S | 3/2019 | Krainer et al. |
| D843,402 S | 3/2019 | Casse et al. |
| D846,590 S | 4/2019 | Cabrera et al. |
| D847,165 S | 4/2019 | Cheney et al. |
| 10,271,766 B1 * | 4/2019 | Parker, Jr. ............ A61B 5/0833 |
| D849,757 S | 5/2019 | Jing et al. |
| 10,278,580 B2 | 5/2019 | Brister et al. |
| 10,898,653 B2 | 1/2021 | Saint et al. |
| 11,369,743 B2 | 6/2022 | Saint et al. |
| 2003/0065536 A1 | 4/2003 | Hansen et al. |
| 2004/0039255 A1 | 2/2004 | Simonsen et al. |
| 2005/0038674 A1 | 2/2005 | Braig et al. |
| 2005/0049179 A1 | 3/2005 | Davidson et al. |
| 2005/0182358 A1 | 8/2005 | Veit et al. |
| 2005/0192494 A1 | 9/2005 | Ginsberg |
| 2005/0192557 A1 | 9/2005 | Brauker et al. |
| 2006/0036144 A1 | 2/2006 | Brister et al. |
| 2006/0173417 A1 | 8/2006 | Rosen et al. |
| 2007/0021715 A1 | 1/2007 | Kohlbrenner et al. |
| 2007/0038044 A1 | 2/2007 | Dobbles et al. |
| 2007/0173708 A9 | 7/2007 | Dobbles et al. |
| 2007/0186923 A1 | 8/2007 | Poutiatine et al. |
| 2007/0239486 A1 | 10/2007 | Gordon |
| 2008/0162192 A1 | 7/2008 | Vonk et al. |
| 2008/0188813 A1 | 8/2008 | Miller et al. |
| 2008/0201169 A1 | 8/2008 | Galasso et al. |
| 2008/0234663 A1 | 9/2008 | Yodfat et al. |
| 2008/0235053 A1 | 9/2008 | Ray et al. |
| 2008/0262469 A1 | 10/2008 | Brister et al. |
| 2009/0036771 A1 | 2/2009 | Fago et al. |
| 2009/0048561 A1 | 2/2009 | Burren et al. |
| 2009/0069742 A1 | 3/2009 | Larsen |
| 2009/0131875 A1 | 5/2009 | Green |
| 2009/0163793 A1 | 6/2009 | Koehler |

(56) References Cited

U.S. PATENT DOCUMENTS

| | | |
|---|---|---|
| 2009/0209938 A1 | 8/2009 | Aalto-Setala |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0299276 A1 | 12/2009 | Brauker et al. |
| 2010/0049126 A1 | 2/2010 | Bronfeld et al. |
| 2010/0063438 A1 | 3/2010 | Bengtsson |
| 2010/0081993 A1 | 4/2010 | O'Connor |
| 2010/0185075 A1 | 7/2010 | Brister et al. |
| 2010/0261987 A1 | 10/2010 | Kamath et al. |
| 2010/0331656 A1 | 12/2010 | Mensinger et al. |
| 2010/0331657 A1 | 12/2010 | Mensinger et al. |
| 2011/0009727 A1 | 1/2011 | Mensinger et al. |
| 2011/0264033 A1 | 10/2011 | Jensen et al. |
| 2011/0270158 A1 | 11/2011 | Brauker et al. |
| 2011/0275986 A1 | 11/2011 | Bashan |
| 2011/0281791 A1 | 11/2011 | Zion et al. |
| 2011/0313349 A1 | 12/2011 | Krulevitch et al. |
| 2011/0313350 A1 | 12/2011 | Krulevitch et al. |
| 2011/0313395 A1 | 12/2011 | Krulevitch et al. |
| 2012/0072236 A1 | 3/2012 | Atkin |
| 2012/0186581 A1 | 7/2012 | Brauker et al. |
| 2012/0190953 A1 | 7/2012 | Brauker et al. |
| 2012/0191063 A1 | 7/2012 | Brauker et al. |
| 2012/0215201 A1 | 8/2012 | Brauker et al. |
| 2012/0220979 A1 | 8/2012 | Brauker et al. |
| 2012/0238852 A1 | 9/2012 | Brauker et al. |
| 2012/0296311 A1 | 11/2012 | Brauker et al. |
| 2013/0035575 A1 | 2/2013 | Mayou et al. |
| 2013/0035865 A1 | 2/2013 | Mayou et al. |
| 2013/0035871 A1 | 2/2013 | Mayou et al. |
| 2013/0171938 A1 | 7/2013 | Mears et al. |
| 2013/0184996 A1 | 7/2013 | Zivitz et al. |
| 2013/0197445 A1 | 8/2013 | Schabbach et al. |
| 2013/0197479 A1 | 8/2013 | Butler et al. |
| 2013/0211248 A1 | 8/2013 | Cowan et al. |
| 2013/0291116 A1 | 10/2013 | Homer |
| 2014/0012117 A1 | 1/2014 | Mensinger et al. |
| 2014/0012118 A1 | 1/2014 | Mensinger et al. |
| 2014/0012510 A1 | 1/2014 | Mensinger et al. |
| 2014/0012511 A1 | 1/2014 | Mensinger et al. |
| 2014/0074041 A1 | 3/2014 | Pedersen et al. |
| 2014/0113856 A1 | 4/2014 | Pohl et al. |
| 2014/0114158 A1 | 4/2014 | Brister et al. |
| 2014/0114161 A1 | 4/2014 | Kamath et al. |
| 2014/0257065 A1 | 9/2014 | Walsh |
| 2014/0276531 A1 | 9/2014 | Walsh |
| 2014/0288494 A1 | 9/2014 | Brister et al. |
| 2015/0073337 A1 | 3/2015 | Saint et al. |
| 2015/0202377 A1 | 7/2015 | Haupt |
| 2015/0351683 A1 | 12/2015 | Brauker et al. |
| 2015/0359965 A1 | 12/2015 | O'Connor et al. |
| 2016/0012205 A1 | 1/2016 | Saint |
| 2016/0030683 A1 | 2/2016 | Taylor |
| 2016/0066843 A1 | 3/2016 | Mensinger et al. |
| 2016/0081632 A1 | 3/2016 | Kamath et al. |
| 2016/0101232 A1 | 4/2016 | Kamath et al. |
| 2016/0175097 A1* | 6/2016 | Chechik ............... A61F 2/004 600/40 |
| 2017/0068799 A1 | 3/2017 | Mensinger et al. |
| 2017/0124272 A1 | 5/2017 | Reihman et al. |
| 2017/0124275 A1 | 5/2017 | Reihman et al. |
| 2017/0124350 A1 | 5/2017 | Reihman et al. |
| 2017/0131993 A1 | 5/2017 | Salameh et al. |
| 2017/0132120 A1 | 5/2017 | Salameh et al. |
| 2017/0185283 A1 | 6/2017 | Bhavaraju et al. |
| 2017/0185284 A1 | 6/2017 | Bhavaraju |
| 2017/0189625 A1 | 7/2017 | Cirillo et al. |
| 2017/0270276 A1 | 9/2017 | Saint et al. |
| 2017/0286194 A1 | 10/2017 | Morris et al. |
| 2017/0286614 A1 | 10/2017 | Morris et al. |
| 2017/0366617 A1 | 12/2017 | Mensinger et al. |
| 2017/0367627 A1 | 12/2017 | Brister et al. |
| 2018/0185587 A1 | 7/2018 | Brauker et al. |
| 2018/0303417 A1 | 10/2018 | Mensinger et al. |
| 2018/0353698 A1 | 12/2018 | Saint et al. |
| 2019/0015020 A1 | 1/2019 | Brister et al. |
| 2019/0035500 A1 | 1/2019 | Saint et al. |
| 2019/0125224 A1 | 5/2019 | Kamath et al. |
| 2019/0132801 A1 | 5/2019 | Kamath et al. |
| 2019/0173885 A1 | 6/2019 | Kamath et al. |

FOREIGN PATENT DOCUMENTS

| | | | |
|---|---|---|---|
| EP | 0927057 A1 | 7/1999 | |
| EP | 2491857 A2 * | 8/2012 | ......... A61B 10/0012 |
| EP | 2572740 A1 | 3/2013 | |
| WO | 9638190 A1 | 12/1996 | |
| WO | 2010052275 A2 | 5/2010 | |
| WO | 2011041007 A1 | 4/2011 | |
| WO | 2012046199 A1 | 4/2012 | |
| WO | 2013053695 A1 | 4/2013 | |
| WO | 2014128157 A1 | 8/2014 | |
| WO | 2015047870 A1 | 4/2015 | |
| WO | 2015169814 A1 | 11/2015 | |
| WO | 2015185686 A1 | 12/2015 | |
| WO | 2016071912 A1 | 5/2016 | |
| WO | 2017132577 A1 | 8/2017 | |

OTHER PUBLICATIONS

Copenheaver, B. R., Authorized Officer, ISA/US, International Search Report and Written Opinion, International Application No. PCT/US2014/056336, dated Dec. 31, 2014, 10 pages.

Young, Lee W., ISA/US, International Search Report, International Application No. PCT/US15/40069, dated Dec. 22, 2015, 13 pages.

Young, Lee W., ISA/US, Invitation to Pay Additional Fees and Partial Search Report, International Application No. PCT/US15/40069, dated Oct. 1, 2015, 2 pages.

Extended European Search Report for European Patent Application No. 14849422.2, dated May 4, 2017, 11 pages.

International Search Report and Written Opinion for PCT Application No. PCT/US2018/036768; dated Aug. 31, 2018, 10 pages.

International Search Report and Written Opinion for PCT Application No. PCT/US2017/15452, dated May 23, 2017, 14 pages.

Extended European Search Report for European Patent Application No. 17745019.4, dated Aug. 6, 2019, 9 pages.

International Search Report and Written Opinion for PCT Application No. PCT/US2018/55646, dated Feb. 6, 2019, 15 pages.

* cited by examiner

Partial Exploded View

3D View

INTELLIGENT MEDICATION DELIVERY SYSTEMS AND METHODS FOR DOSE SETTING AND DISPENSING MONITORING

CROSS-REFERENCE TO RELATED APPLICATIONS

This application is a continuation of U.S. patent application Ser. No. 17/156,681, filed on Jan. 25, 2021, now U.S. Pat. No. 11,369,743, which is a continuation of U.S. patent application Ser. No. 16/407,046, filed on May 8, 2019, now U.S. Pat. No. 10,898,653, which claims the benefit of the filing date of provisional U.S. Patent Application No. 62/668,723, filed on May 8, 2018.

INTRODUCTION

This disclosure relates to medicine administering and tracking systems, devices, and processes.

BACKGROUND

Diabetes mellitus, also referred to as diabetes, is a metabolic disease associated with high blood sugar due to insufficient production or use of insulin by the body. Diabetes is widely spread globally, affecting hundreds of millions of people, and is among the leading causes of death globally. Diabetes has been categorized into three categories or types: type 1, type 2, and gestational diabetes. Type 1 diabetes is associated with the body's failure to produce sufficient levels of insulin for cells to uptake glucose. Type 2 diabetes is associated with insulin resistance, in which cells fail to use insulin properly. The third type of diabetes is commonly referred to as gestational diabetes, which can occur during pregnancy when a pregnant woman develops a high blood glucose level. Gestational diabetes can develop into type 2 diabetes, but often resolves after the pregnancy.

SUMMARY

Systems, devices, and techniques are disclosed for administering and tracking medicine to patients and providing health management capabilities for patients and caregivers.

In some aspects, an intelligent medicine administering system includes a medicine injection device having a multi-channel, mechanical encoder that detects fault conditions (e.g., such as open or short circuits) and a patient user's companion device including a software application operable to implement algorithms for detecting faults and communication loss and alerting the patient user for safety and fail-safes of the medicine injection device.

In some aspects, a system for administering insulin to a patient includes an injection pen device, the injection pen device structured to contain a medicine cartridge and include a dose setting mechanism to set a dose of insulin stored in the medicine cartridge to be dispensed by the injection pen device, a dispensing mechanism to dispense the insulin according to the set dose, a sensor unit to detect a dispensed dose, an electronics unit including a processor, a memory, and a wireless transmitter, the electronics unit configured to process the detected dispensed dose with time data associated with a dispensing event to generate dose data, and to wirelessly transmit the dose data, and a multi-channel encoder, in communication with the electronics unit and one or both of the dose setting mechanism and the dispensing mechanism, to monitor a dose setting operation or a dose dispensing operation; and the injection pen device in wireless communication with a mobile communication device that includes a data processing unit including a processor and memory to receive and process the dose data, wherein one or both of the electronics unit of the injection pen device or the data processing unit of the mobile communication device are configured to determine a fault in an operation of the injection pen device indicative of an error based on a quality of signal from the multi-channel encoder, wherein the fault is determined based on a signal quality analysis of at least one of electrical noise, signal frequency error, phase error, or duty cycle error.

In some aspects, a multi-channel encoder for an insulin injection device includes a first component including a substrate and a pattern of electrically conductive segmented contact pads in a first region of the substrate, and a plurality of channel pads disposed on the substrate in a second region, the plurality of channel pads including an electrical ground pad and at least three input channel pads; and a second component including an electrically conductive sweeping contact that electrically interfaces with individual segmented contact pads of the first component, one at a time, during the sweep of the pattern, wherein the second component is configured to rotate about a shared axis with the first component, or vice versa, such that the sweeping contact sweeps along the pattern of segmented contact pads during rotation wherein the multi-channel encoder is in communication with a processing unit of the insulin injection device.

DETAILED DESCRIPTION

Figure 1A:
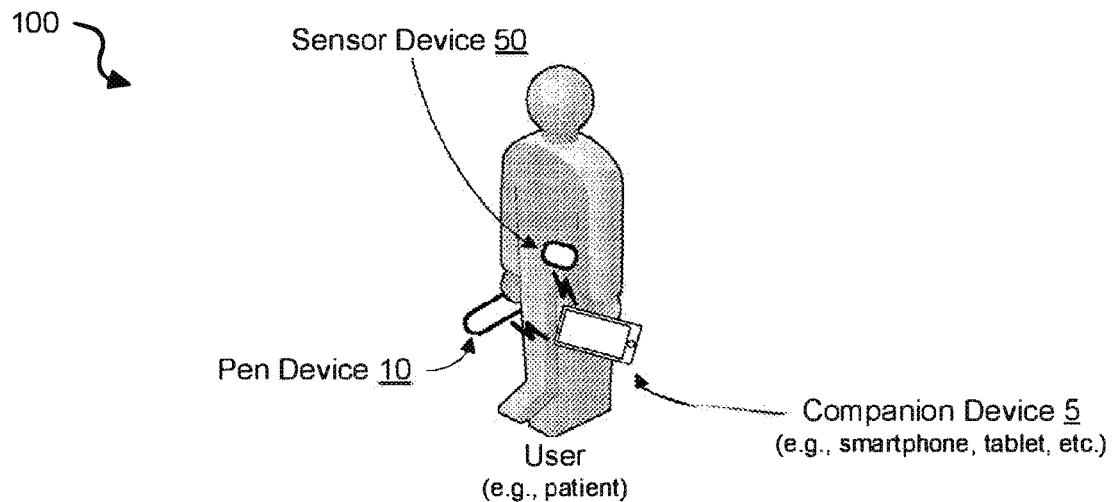
FIG. 1A shows a diagram of an example embodiment of an intelligent medicine administering system in accordance with the present technology.

Various diseases and medical conditions, such as diabetes, require a patient to self-administer doses of a fluid medication. Typically, when administering a fluid medication, the appropriate dose amount is set and dispensed by the patient using a syringe, a pen, or a pump. For example, self-administered medicaments or medicine include insulin used to treat diabetes, Follistim® used to treat infertility, or other injectable medicines such as Humira®, Enbrel®, Lovenox® and Ovidrel®, or others.

A medicament pen is a device that can be used to inject a quantity of a medicine (e.g., single or multiple boluses or doses of the medicine) into a user's body, where more than one dose can be stored in a medicine cartridge contained in the pen device. Pens offer the benefit of simplicity over other methods of delivery, such as syringe or pump-based methods. For example, syringes typically require more steps to deliver a dose, and pumps typically are more complicated to use and require a constant tether to the patient. However, previously there has not been an automated way to track and communicate the doses given with the pen in a simple, effective and reliable manner. In addition, it can be difficult to know how much to dose with the pen, when to dose, or if the patient dosed at all.

As with the dosing of any medication, it is sometimes hard for a patient to remember if a dose has been given. For this reason, for example, pill reminders have been developed where the patient places the medication for the day in a cup labeled with that day. Once they take their medication, there is no question it has been taken because the pills are no longer in the cup. Yet, there are no widely acceptable solutions that address this problem for injection-based therapies. Therefore, without simple, effective and reliable ways of tracking medicine doses, particularly for managing lifelong or chronic conditions like diabetes, patients may easily miss a dose or administer an incorrect dose (e.g., under-dose or over-dose) of their medicine which may result in serious, dangerous consequences to their health.

In addition to the challenges of tracking doses, calculating the right dose at the right time or under the right conditions is a widespread problem for patients of chronic conditions requiring daily dosing of medicine. Conventional dose calculators for administering insulin for Type I and Type II diabetes typically require manual estimation of carbohydrates ("carbs") at mealtime. For some users, carb counting and estimating may be too difficult, and some users may not utilize the dose calculator due to the manual work and number of steps required to do so, e.g., taking out one's smartphone, opening up an app, manually typing calculator inputs, etc.

Systems, devices, and techniques are disclosed for administering and tracking medicine to patients and providing health management capabilities for patients and caregivers, which include a medicine injection device having a multi-channel, mechanical encoder that detects fault conditions (e.g., such as open or short circuits) and a patient user's companion device including a software application operable to implement algorithms for detecting faults and communication loss and alerting the patient user for safety and fail-safes of the medicine injection device.

In some embodiments in accordance with the present technology, an intelligent medicine administering system provides medicine dose recommendation and management capabilities for Type I and Type II diabetes patients and their caregivers. In some aspects, the system includes a medicine injection device (e.g., insulin pen, also referred to as a "pen" or "pen device"), in wireless communication with a patient's companion device (e.g., smartphone). The companion device includes a software application ("app") having a dose calculator and decision support modules to calculate and recommend the dose of a medicine (e.g., insulin) the patient should administer using the wirelessly connected medicine injection device, as well as to provide control over several functionalities of the injection device, e.g., such as monitoring and recording dose sizes dialed on the injection device.

Communication between the pen device and the companion device provides the ability for dose tracking, logging, calculating, recommending, and/or communicating dose data with a user (e.g., patient user, health care provider (HCP) and/or caregiver), and other advantages of the intelligent medicine administering system. For example, each bolus that is dispensed by the pen device can be automatically logged and communicated to the companion device.

FIG. 1A shows a diagram of an example embodiment of an intelligent medicine administering system 100 in accordance with the present technology. The system 100 includes a pen device 10 in wireless communication with a mobile computing and communication device 5 of a patient user, also referred to as the user's companion device. The pen device 10 is operable to select, set and/or dispense a dose of the medicine for dispensing. In some implementations, the companion device 5 includes a smartphone, tablet, and/or wearable computing device, such as a smartwatch, smartglasses, etc. In some implementations, the companion device 5 is in communication with other computing devices, such as a laptop and/or desktop computer, a smart television, or network-based server computer. The companion device 5 includes an app associated with the pen device 10 of the intelligent medicine administering system 100, which can monitor and/or control functionalities of the pen device 10 and to provide a dose calculator and/or decision support modules that can calculate and recommend a dose of the medicine for the patient user to administer using the pen device 10.

The companion device 5 can be used to obtain, process and/or display contextual data that can be used to relate to the patient user's health condition, including the condition for which the pen device 10 is used to treat. In an illustrative example, the companion device 5 is operable to track the patient user's location; the patient user's physical activity including step count, movement distance and/or intensity, estimated calories burned, and/or activity duration; and/or the patient user's interaction pattern with the companion device 5. The app associated with the system 100 can aggregate and process the contextual data to generate decision support outputs to guide and aid the patient user in using the pen device 10 and/or managing their behavior to promote better health outcomes in treating his/her health condition.

In some embodiments, the system 100 includes a sensor device 50 to monitor one or more health metrics of the patient user. Examples of health metric data monitored by the sensor device 50 include analytes, such as glucose, heart rate, blood pressure, user movement, or other. In some implementations, the sensor device 50 is a wearable sensor device such as a continuous glucose monitor (CGM) to obtain transcutaneous or blood glucose measurements that are processed to produce continuous glucose values. For example, the continuous glucose monitor can include a glucose processing module implemented on a stand-alone display device and/or implemented on the companion device 5, which processes, stores and displays the continuous glucose values for the patient user.

Figure 1B:
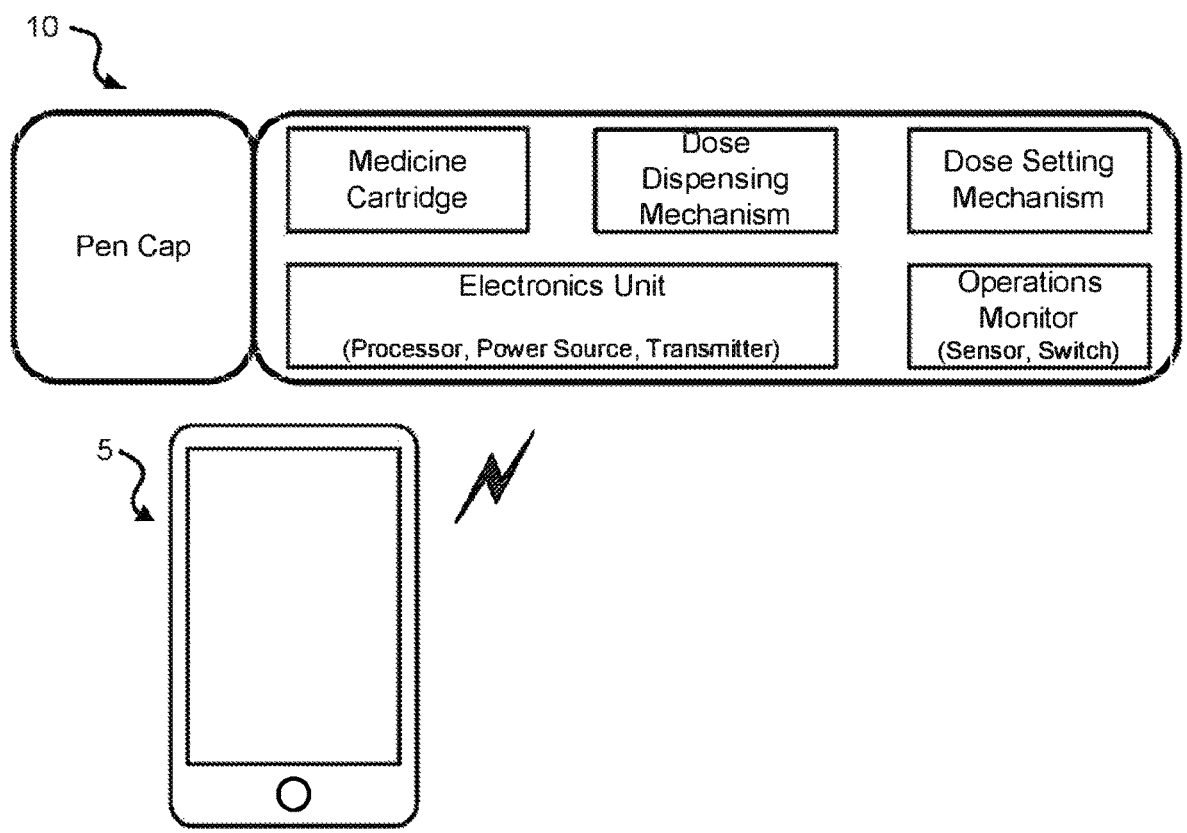
FIG. 1B shows a diagram of an example embodiment of a pen device of the intelligent medicine administering system of FIG. 1A.

FIG. 1B shows a diagram of an example embodiment of the pen device 10 of the intelligent medicine administering system 100. The pen device 10 is structured to have a body which contains the medicine cartridge (e.g., which can be replaceable). The pen device 10 is structured to include a dose dispensing mechanism to dispense (e.g., deliver) the medicine contained in the medicine cartridge out of the pen device; a dose setting mechanism to select and/or set the dose to be dispensed; an operations monitoring mechanism to determine that the pen device is being operated and/or to monitor the operation of the dose being dispensed (e.g., such as a switch and/or sensor, or an encoder); and an electronics unit that can include a processor, a memory, a battery or other power source, and a transmitter.

The pen device 10 is configured in communication with the patient user's mobile computing and communication device 5, e.g., such as the user's smartphone, tablet, and/or wearable computing device, such as a smartwatch, smartglasses, etc. and/or a user's laptop and/or desktop computer, a smart television, or network-based server computer.

In some implementations of the system 100, for example, to use the pen device 10, the user first dials up a dose using a dose knob. The dose knob of the pen device 10 can be included as part of the dose setting mechanism and/or the dose dispensing mechanism. For example, the dose may be adjusted up or down prior to administration of the dose. When the user applies a force against a dose dispensing button (e.g., presses against the dose dispensing button that is caused to protrude outward from the pen's body upon dialing the dose using the dose knob), a pushing component (e.g., also referred to as a 'plunger') of the dose dispensing mechanism is depressed against an abutment of the medicine cartridge loaded in the pen device 10 to cause the pen device 10 to begin to dispense the medicine, in which the quantity dispensed is in accordance with that set by the dose setting mechanism. In such implementations, the operations monitoring mechanism of the pen device 10 will begin to sense movement of a rotating component or shaft that drives the plunger, for example, in which the movement is sensed through an encoder. In some examples, the encoder can be configured to sense the rotation of a component that is coupled to the drive shaft, and as the drive shaft rotates the plunger moves linearly; and therefore by sensing rotation of the component, the movement of the drive shaft and the plunger is sensed. Movement of the encoder may be detected as data processed by a processor of the electronics unit of the pen device 10, which can be used to measure the dose. In some implementations, the processor can then store the size of the dose along with a time stamp for that dose. In some implementations, the pen device 10 can then transmit the dose and related information to the companion device 5. In such implementations when the dose is transmitted, the data associated with the particular transmitted dose is marked in the memory of the pen device 10 as transmitted. In such implementations if the dose was not yet transmitted to the companion device 5, then the data associated with the dose will be transmitted at the next time a successful communication link between the pen device 10 and the companion device 5 is established.

The operations monitoring mechanism of the pen device 10 can include a sensor that can utilize any method of sensing rotary or linear movement. Non-limiting examples of such sensors include rotary and linear encoders, Hall effect and other magnetic based sensors, linearly variable displacement transducers, or any other appropriate method of sensing known in the art.

The dose dispensing mechanism of the pen device 10 can include a manually powered mechanism or a motorized mechanism. In either case, a force (e.g., either produced by the patient or by an electrically-powered motor) pushes on the plunger of the dose dispensing mechanism to in turn force a receiving plunger of the medicament vial or cartridge to deliver the specific amount of the medicament. In some implementations, for example, the dose dispensing mechanism can be adjusted to deliver the dose over a different period of time. In one example, the dose dispensing mechanism can be operated such that the plunger is pushed in by an adjustable tension spring or change the speed of the motor to inject the dose over a time frame (e.g., 1 s, 5 s or other) to aid in reducing the pain of dosing. In one example, the dose dispensing mechanism can be operated over a much longer period of time, e.g., to better match the dynamics of carbohydrates, which can be like an extended bolus with a pump.

The software application (app) of the companion device 5 associated with the pen device 10 provides a user interface to allow the user to manage his/her health related data. In some implementations, for example, the companion device 5 can be configured to control some functionalities of the pen device 10. In some implementations, for example, the companion device 5 includes the user's existing smartphone, tablet, or wearable computing device. In some implementations, for example, the companion device 5 is an independent portable device that the user may carry on his/her person. In one example embodiments of an independent portable companion device 5, the companion device 5 includes a data processing unit, wireless communication unit to allow the device to communicate with the pen device 10, and a display unit.

Figure 1C:
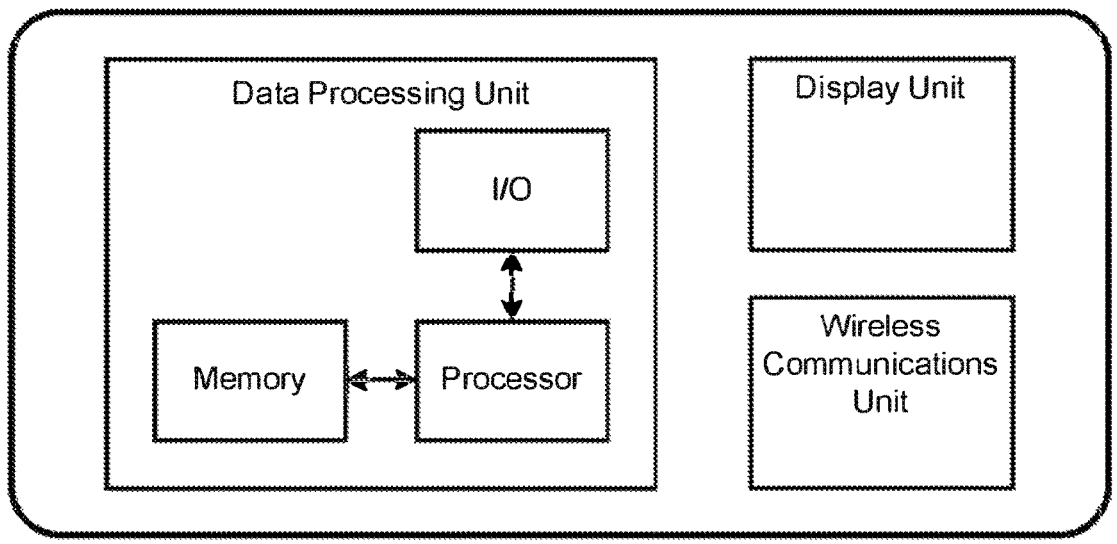
FIG. 1C shows a block diagram of an example embodiment of the companion device of the intelligent medicine administering system of FIG. 1A.

FIG. 1C shows a block diagram of an example embodiment of the companion device 5 of the intelligent medicine administering system 100. The data processing unit of the companion device 5 includes a processor to process data, a memory in communication with the processor to store data, and an input/output unit (I/O) to interface the processor and/or memory to other modules, units or devices of the companion device 5 or external devices. For example, the processor can include a central processing unit (CPU) or a microcontroller unit (MCU). For example, the memory can include and store processor-executable code, which when executed by the processor, configures the data processing unit to perform various operations, e.g., such as receiving information, commands, and/or data, processing information and data, and transmitting or providing information/data to another device. In some implementations, the data processing unit can transmit raw or processed data to a computer system or communication network accessible via the Internet (referred to as 'the cloud') that includes one or more remote computational processing devices (e.g., servers in the cloud). To support various functions of the data processing unit, the memory can store information and data, such as instructions, software, values, images, and other data processed or referenced by the processor. For example, various types of Random Access Memory (RAM) devices, Read Only Memory (ROM) devices, Flash Memory devices, and other suitable storage media can be used to implement storage functions of the memory unit. The I/O of the data processing unit can interface the data processing unit with the wireless communications unit to utilize various types of wired or wireless interfaces compatible with typical data communication standards, for example, which can be used in communications of the data processing unit with other devices such as the pen device 10, via a wireless transmitter/receiver (Tx/Rx) unit, e.g., including, but not limited to, Bluetooth, Bluetooth low energy, Zigbee, IEEE 802.11, Wireless Local Area Network (WLAN), Wireless Personal Area Network (WPAN), Wireless Wide Area Network (WWAN), WiMAX, IEEE 802.16 (Worldwide Interoperability for Microwave Access (WiMAX)), 3G/4G/LTE cellular communication methods, NFC (Near Field Communication), and parallel interfaces. The I/O of the data processing unit can also interface with other external interfaces, sources of data storage, and/or visual or audio display devices, etc. to retrieve and transfer data and information that can be processed by the processor, stored in the memory unit, or exhibited on an output unit of the companion device 5 or an external device. For example, a display unit of the companion device 5 can be configured to be in data communication with the data processing unit, e.g., via the I/O, to provide a visual display, an audio display, and/or other sensory display that produces the user interface of the software application of the disclosed technology for health management. In some examples, the display unit can include various types of screen displays, speakers, or printing interfaces, e.g., including but not limited to, light emitting diode (LED), or liquid crystal display (LCD) monitor or screen, cathode ray tube (CRT) as a visual display; audio signal transducer apparatuses as an audio display; and/or toner, liquid inkjet, solid ink, dye sublimation, inkless (e.g., such as thermal or UV) printing apparatuses, etc.

In various operations of the intelligent medicine administering system 100, for example, when a dosing event (e.g., an amount of fluid is dispensed from the pen device 10), a time stamp associated with the dispensing is referenced is recorded by the processing unit of the pen device 10 (e.g., stored in the memory of the pen device 10). For example, the time stamp may be the current time or a time where a count-up timer is used. When the dose information is eventually transmitted to the companion device 5, the time stamp and/or a 'time-since-dose' parameter is transmitted by the pen device 10 and received by the companion device 5 and stored in the memory of the data processing unit of the companion device 5. In some implementations, for example, the time of the dose can be determined without the pen having to know the current time. This can simplify operation and setup of the pen device 10. In some implementations, for example, a user time is initialized on the pen device 10 from the companion device 5, in which the user time is used for dose time tracking. Using the system 100, the companion device 5 can know the time of the dose relative to the current time.

Once the companion device 5 receives the dose related information (e.g., which can include the time information and dose setting and/or dispensing information, and other information about the pen device 10 related to the dosing event), the companion device 5 stores the dose related information in memory, e.g., which can include among a list of doses or dosing events. For example, via the software application's user interface, the companion device 5 allows the patient to browse a list of previous doses, to view an estimate of current medicament active in the patient's body ("medicament on board") based on calculations performed by a medicine calculation module of the software application, and/or to utilize a dose calculation module of the software application to assist the patient regarding dose setting information on the size of the next dose to be delivered. For example, the patient could enter carbohydrates to be eaten, current blood sugar, and the companion device 5 would already know insulin on board. Using these parameters a suggested medicine dose (e.g., such as insulin dose), calculated by the dose calculation module, may be determined. In some implementations, for example, the companion device 5 can also allow the patient to manually enter boluses into the pen device 10 or another medicine delivery device. This would be useful if the patient was forced to use a syringe, or if the battery in the pen device 10 was depleted.

Example embodiments and implementations of the disclosed intelligent medicine administering system, including a medicine injection device (e.g., pen device) in communication with a companion device, are described herein. Some examples of features of an intelligent medicine administering system that can be used with the example devices, systems, and methods for monitoring dose settings and dispensing operations are described in U.S. Pat. No. 9,672,328 B2, entitled "Medicine Administering System Including Injection Pen and Companion Device," the entire content of which is incorporated by reference in this disclosure.

While the disclosed embodiments described herein are primarily based on diabetes management systems and methods involving insulin pen and glucose monitoring devices to facilitate understanding of the underlying concepts, it is understood that the disclosed embodiments can also include treatment of other health conditions using other medications by the pen device and/or monitoring of other analytes by sensor devices.

Robust Dose Measurement and Tracking Device for Medicine Dispensing Device

In a drug delivery device, such as a smart insulin pen, the amount of drug delivered may be measured by quantifying mechanism rotation with a rotary encoder.

A conventional two-channel quadrature encoder has two channels with only four possible states, all of which are valid, i.e., [00], [10], [01], and [11], and which occur in order as the encoder rotates and in the reverse order when the encoder rotated in the opposite direction. These signals are generated as electrical contacts sweep across a conductive pattern with alternating segments of conductive and non-conductive areas. In principle, when a contact touches a conductive area, it outputs a "1", and when it disconnects and is in a nonconductive area it outputs a "0". However, a short circuit caused by damage or liquid ingress will appear as [11] and an open circuit caused by damage or contamination will appear as [00]. However, since these are valid normal states, no error would be detected by this conventional two-channel encoder. Instead, for example, it would just appear that the encoder was not moving. Where an encoder is placed to detect medicine dose size (such as in a smart insulin pen), this would incorrectly indicate that no dose was taken.

In various uses of conventional encoders, typically the encoder pattern is connected to electrical ground and the inputs are pulled high via a pull-up resistor; but, in any of the examples the polarity could be reversed or voltage levels changed. All that is required is that there is a voltage differential between the pattern and the input contacts, so that connection with the pattern can be detected. The assignment of 0 or 1 to connected/disconnected or high/low voltage can also be arbitrarily defined for each application.

These and other limitations of conventional encoders for use in accuracy-critical devices, like medicine dispensing devices, create dangerous risks to the end users of such devices. Therefore, medicine dispensing device would greatly benefit from newer designs and data processing schemes to ensure valid states of an encoder are indicative of the performance accuracy of the medicine dispensing device.

Example embodiments of a multi-channel, mechanical encoder for a medicine dispensing device (such as pen device 10) are described for detecting fault conditions (e.g., such as open or short circuits) and improving the accuracy of dose setting and dispensing tracking capabilities of the medicine dispensing device. Furthermore, example embodiments of methods which can be implemented using a software application on the medicine injection device and/or a corresponding companion device are described for detecting fault conditions of encoders and the loss of communications to and/or alerting of the patient user in events of damage or other causes that affect signal quality of a mechanical encoder and lead to erroneous results.

Figure 1D:
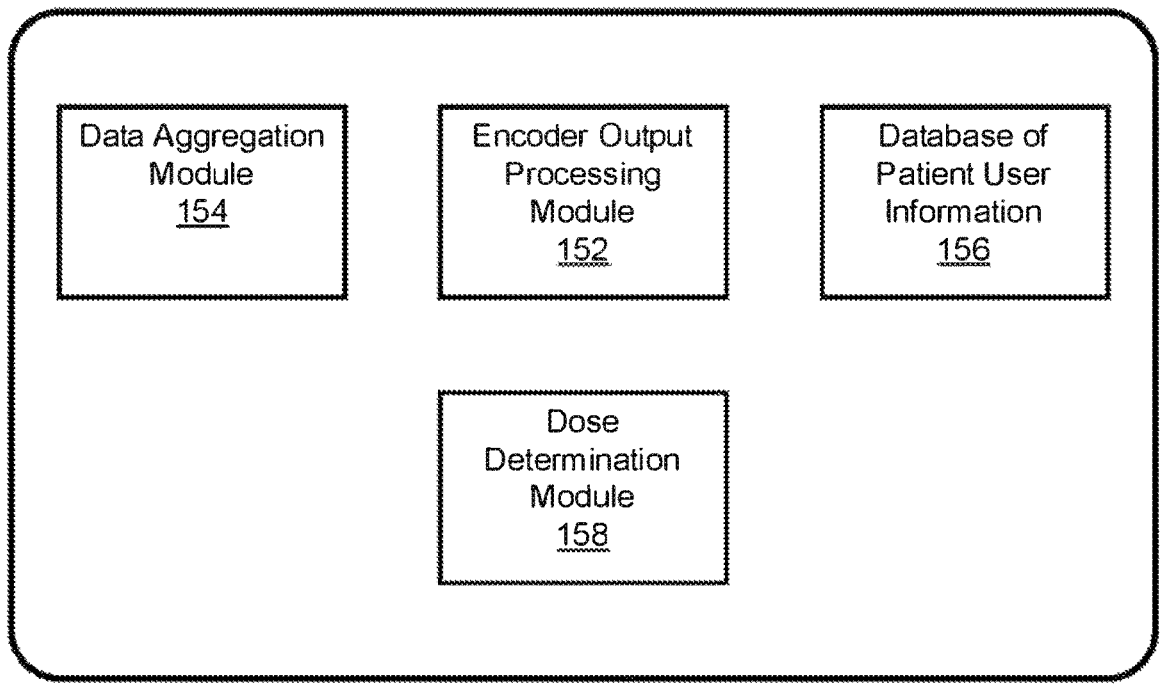
FIG. 1D shows a block diagram of an example software architecture of data processing modules in some example embodiments of the app of the intelligent medicine administrating system of FIG. 1A.

FIG. 1D shows a block diagram of an example software architecture of data processing modules, labeled 150, in accordance with certain example embodiments of the app of the intelligent medicine administrating system 100. In some embodiments, the software architecture 150 includes data processing modules embodied as part of the app resident on the companion device 5. In some embodiments of the software architecture 150 of the system 100, some or all of the data processing modules are resident on the pen device 10, e.g., resident in the electronics unit. In some embodiments of the software architecture 150, some or all of the data processing modules are resident on the companion device 5, e.g., resident in the data processing unit. The data processing modules of the app on the companion device 5 may be include different or the same data processing modules of the software architecture 150 resident on the pen device 10. Similarly, in some embodiments, for example, the software architecture 150 can be embodied as part of a data processing system in the cloud (e.g., resident on one or more cloud computers). In some embodiments, the software architecture 150 is embodied as part of both the software app on the companion device 5 and the data processing system in the cloud, in which some or all of the modules of the software architecture 150 are shared or divided among the app on the companion device 5 and the data processing system in the cloud.

In various implementations, the software architecture 150 processes the data from the pen device 10, associated with the detected and/or pre-processed output signals of an encoder configured on the pen device 10. In some embodiments, one of the data processing modules of the software architecture 150 includes an encoder output processing module 152 to receive and process the output signals received by the encoder. The encoder output processing module 152 is able to monitor the 'health' of the pen device 10 to detect false positives or missed negatives associated with the output of the encoder, which monitors operations of the dose setting and/or dispensing mechanisms of the pen device. For example, conventional encoders are susceptible to nondetection of liquid ingress in the pen, e.g., due to indication of valid state [11], and nondetection of damage of the pen, e.g., due to a detection of valid state [00]. The encoder output processing module 152 is capable of interrogating the output signals of the encoder, e.g., including that of conventional encoders, in a manner that can distinguish additional information in the output signals and identify such detrimental conditions of the pen device, like liquid ingress or mechanical or electrical damage. Additionally, the encoder output processing module 152 is configured to detect and alert the patient user of faults in pen device, and/or to determine loss of communications and alerting the patient user accordingly. Fault conditions of the pen device can include a mechanically damaged/disconnected electrical contact or connection of the encoder, excessive contact wear and/or mechanism wear affecting proper alignment of components of the encoder, liquid intrusion (e.g., of water, insulin, or other conductive liquid) into the encoder, and/or corrosion, particulate or foreign material contamination of the encoder.

The software architecture 150 may also be configured to process health metric data and contextual data obtained by the app on the companion device 5, from the pen device 10, from the sensor device 50, and/or from other devices of the patient user and/or apps on the companion device 5. In some embodiments, for example, the software architecture 150 includes a data aggregator module 154 to obtain the health metric data from a device, such as the pen device 10, sensor device 50, and/or other devices or apps in communication with the companion device 5. The software architecture 150 includes or is in communication with a database 156 to store the health data and contextual data associated with the patient user and populations of patient users In some embodiments, the software architecture 150 includes a dose determination module 158, such as a dose calculator module, to autonomously calculate a dose of the medicine associated with dose injections from the pen device 10 based on time-relevant and context or circumstances-relevant data specific to the patient user of the pen device 10. The example modules shown in the software architecture diagram can be organized to provide data to one another in various ways, including directly (e.g., module-to-module) and/or indirectly (e.g., via an intermediary module), based on a periodic, an intermittent, and/or a per-request basis.

Quantification of Signal Quality from Encoder Output

A well-functioning encoder should have distinct rising and falling edges in its signal, and for example, with minimal bounce, no erratic spikes or high-frequency transitions, and edges in the proper sequence for the direction of encoder rotation.

In some implementations of an intelligent medicine administering system 100 including the example encoder output processing module 152, the system 100 includes a quantitative encoder signal analysis algorithm to detect and quantify the signal quality of an encoder in a dispensing device, such as a medicament pen device, e.g., identifying if there is a poor signal quality of the encoder. In some embodiments, the quantitative encoder signal analysis algorithm can be resident in the encoder output processing module 152 of the app, as illustrated in the example of FIG. 1D. For example, implementations of the algorithm can indicate premature wear, dirt ingress, corrosion, physical damage, or other causes that affect signal quality of a mechanical encoder and lead to erroneous results. Also, for example, by detecting these conditions early, a user can be warned and/or a device can be disabled to avoid reaching the point of sending incorrect measurements. Noise can be quantified in implementations of the quantitative encoder signal analysis algorithm, such that the algorithm produces an output used to trigger a fault over a defined threshold of severity or frequency of noise in the encoder signal.

In various embodiments, the quantitative encoder signal analysis algorithm includes a process to detect the rising portions (e.g., signal portion that trends upward from "0" to "1" or points therebetween) and falling portions (e.g. signal portion that trends downward from "1" to "0" or points therebetween). The algorithm includes a process to quantitatively analyze the rising and falling portions. In some embodiments of the quantitative encoder signal analysis algorithm, the quantitative analytical process examining one or more of the frequency, phase, duty cycle and/or resistance of the signal to quantify and characterize noise in the mechanical encoder, which is used to affect (e.g., detect or correct potential problems in) the performance of the encoder and validate results by the encoder. The output of the algorithm can include a binary result (e.g., valid or invalid), or other output characterizing the signal.

Implementations of the quantitative encoder signal analysis algorithm are beneficial to an encoder used on devices like a medicament delivery pen due to the design and configuration of the dose setting and/or dispensing mechanisms of such pen devices. For example, other encoders, like on a volume knob of a stereo, might very well be turned erratically in both directions at varying speed. However, this is a highly unlikely, if not impossible, scenario for medicament dispensing devices because such devices have certain mechanical constraints. These constraints provide can be accounted for in the quantitative encoder signal analysis algorithm to allow the detections of detrimental conditions of the pen that conventional encoders may fail to identify. As an example, in pen devices, any movement is typically a single continuous rotation in a single direction. The quantitative encoder signal analysis algorithm thereby can account for this operation in at least some of the detection modes described below.

Figure 2A:
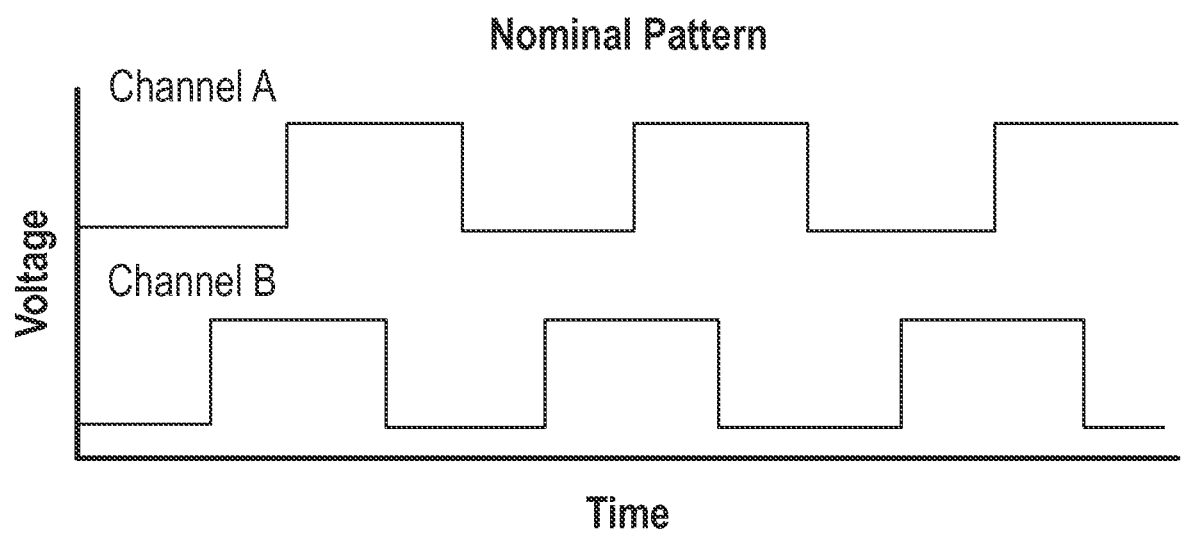
FIGS. 2A-2E show voltage-time plots of various example outputs of a mechanical encoder's electrical output to illustrate the noise quantification techniques by an example embodiment of a quantitative encoder signal analysis algorithm in accordance with the present technology.

FIGS. 2A-2E show voltage-time plots of various example outputs of a mechanical encoder's electrical output to illustrate the noise quantification techniques by the quantitative encoder signal analysis algorithm. FIG. 2A shows an example voltage-time plot featuring a normal or nominal pattern on the two channels (channel A and channel B) of an example two-channel quadrature encoder.

Figure 2B:
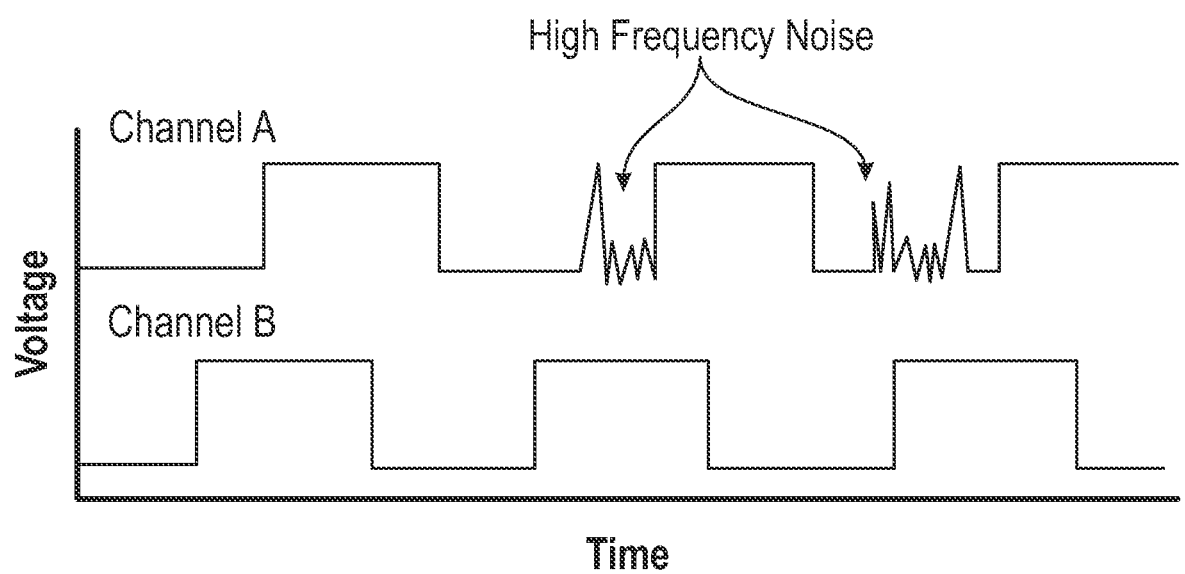

Frequency analysis: The algorithm can be used to analyze frequency of the encoder signal. For example, the algorithm can identify noise in the encoder, which, given the physical constraints of the encoder's maximum speed, the electrical signal output of the encoder that exceeds the maximum speed is indicative of erratic noise. FIG. 2B shows an example voltage-time plot featuring high frequency noise on one of the channels (channel A) of an example encoder. In this example, the frequency in the rising and falling signal of the encoder is monitored by the algorithm, and when the encoder produces a signal in which the frequency of the rising and falling passes a predetermined threshold, e.g., exceeds a maximum frequency value, then the algorithm can identify a fault occurred by the encoder, such as illustrated in FIG. 2B. For example, the threshold can be a value or range based on empirical or precomputed data values.

Figure 2C:
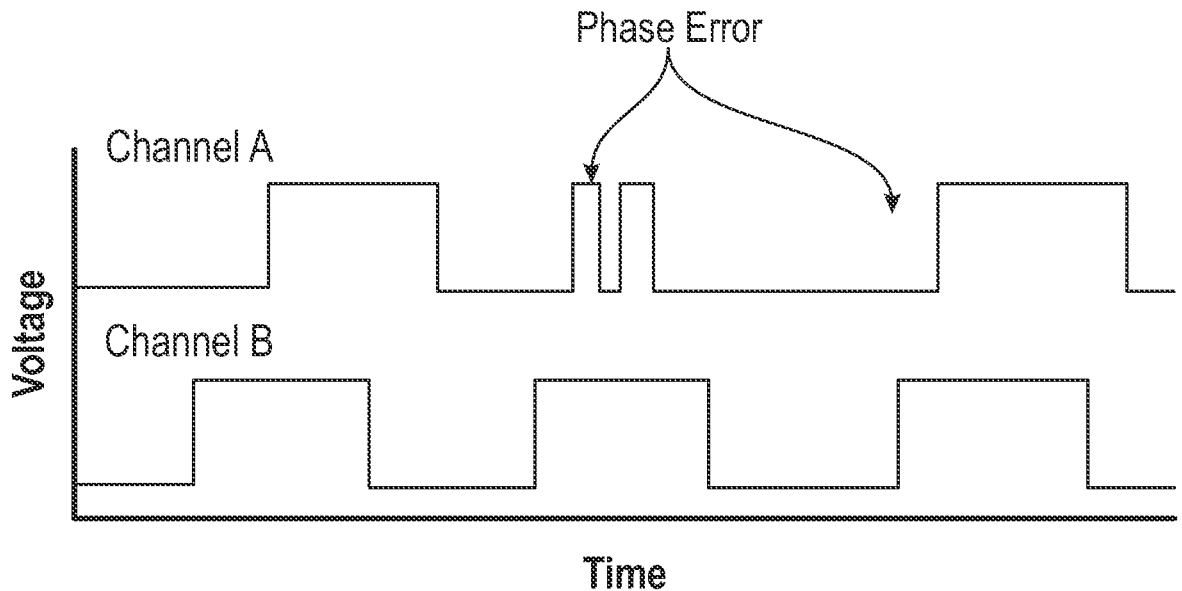

Phase analysis: The algorithm can be used to analyze phase of the encoder signal. For example, the algorithm can identify noise in the encoder, in which, for a given direction of rotation, there is a single correct sequence of encoder edges. If edges are observed out of the usual order, it indicates a problem. FIG. 2C shows an example voltage-time plot featuring phase error indicative of noise on one of the channels (channel A) of an example encoder. The phase in the rising edge or falling edge of samples of the encoder signal is monitored by the algorithm. In this example, the rising edge of the signal in two instances is determined to be out of phase based on a predetermined phase pattern, such that the algorithm can identify a fault occurred by the encoder, such as illustrated in FIG. 2C.

Figure 2D:
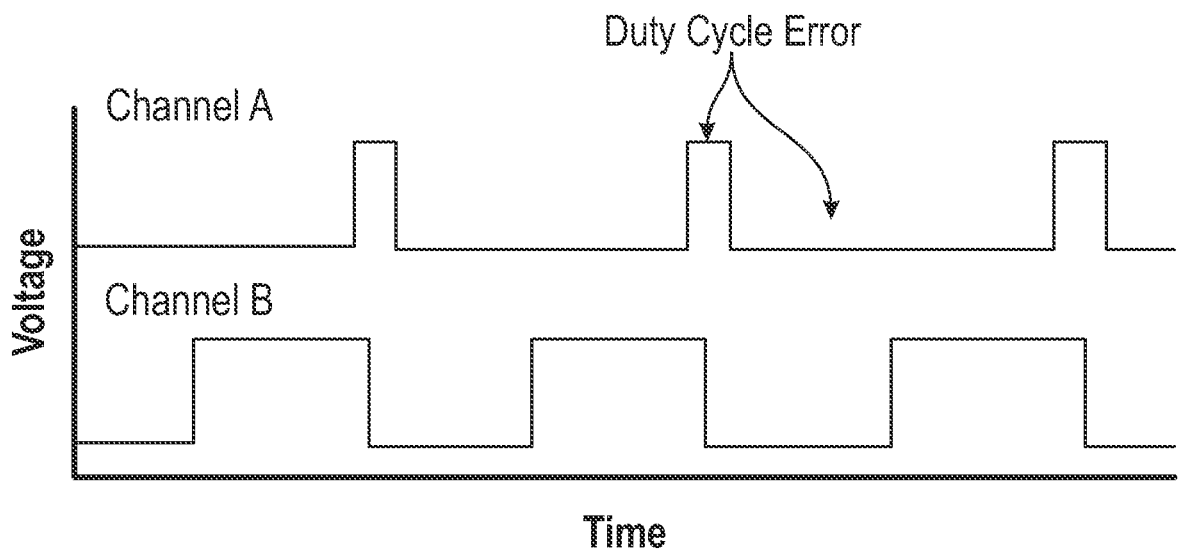

Duty cycle: The percent of the time an encoder switch is connected is called the duty cycle. At a constant rotational speed, the duty cycle for a particular encoder is fixed by the conductive pattern strip spacing. In some applications, the duty cycle should be 50%, indicating that the contact is connected for as much time as it is disconnected. If the contact wears, creating a wider contact patch, that will increase the duty cycle. If the pattern gets contaminated at the edges, covering part of the pattern, that may decrease the duty cycle. The algorithm can be used to analyze duty cycle of the encoder signal to identify noise associated with a fault in the encoder. In an example of a pen device, a manual pen will not rotate at exactly a fixed speed, but by averaging the duty cycle observed over several cycles of the encoder, e.g., possibly over several doses over time, the actual duty cycle can be roughly calculated. If it exceeds a preset threshold, or preset amount of drift from the initial value, the algorithm produces an output indicative of a problem with the encoder based on the duty cycle of the signal. For example, the threshold can be a value or range based on empirical or precomputed data values. FIG. 2D shows an example voltage-time plot featuring duty cycle error indicative of noise on one of the channels (channel A) of an example encoder.

Figure 2E:
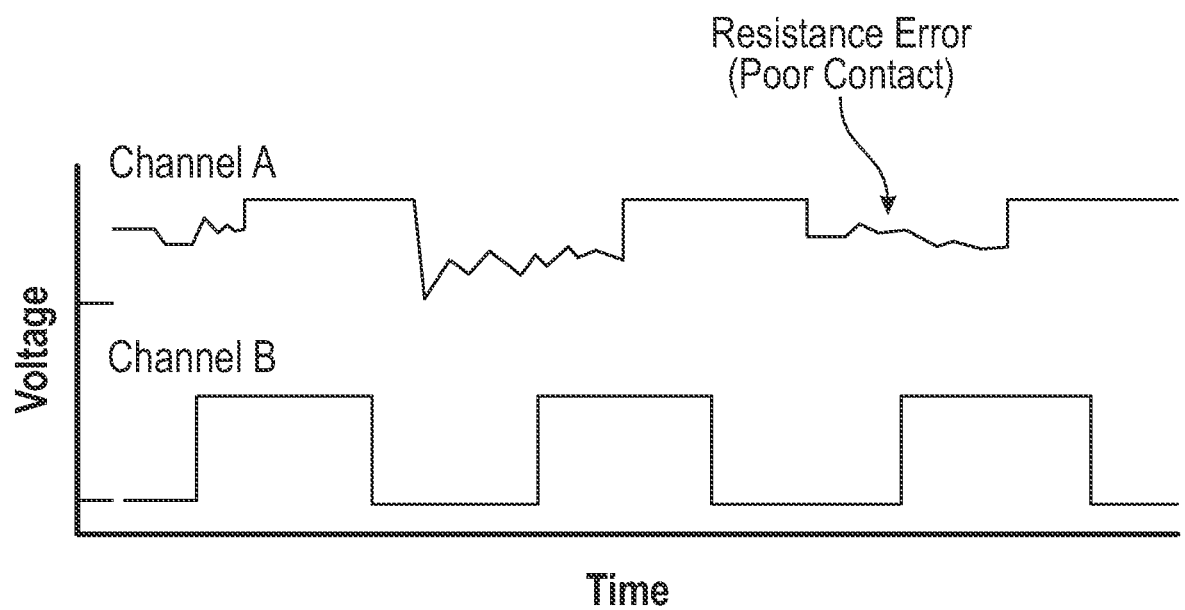
Figure 2E:
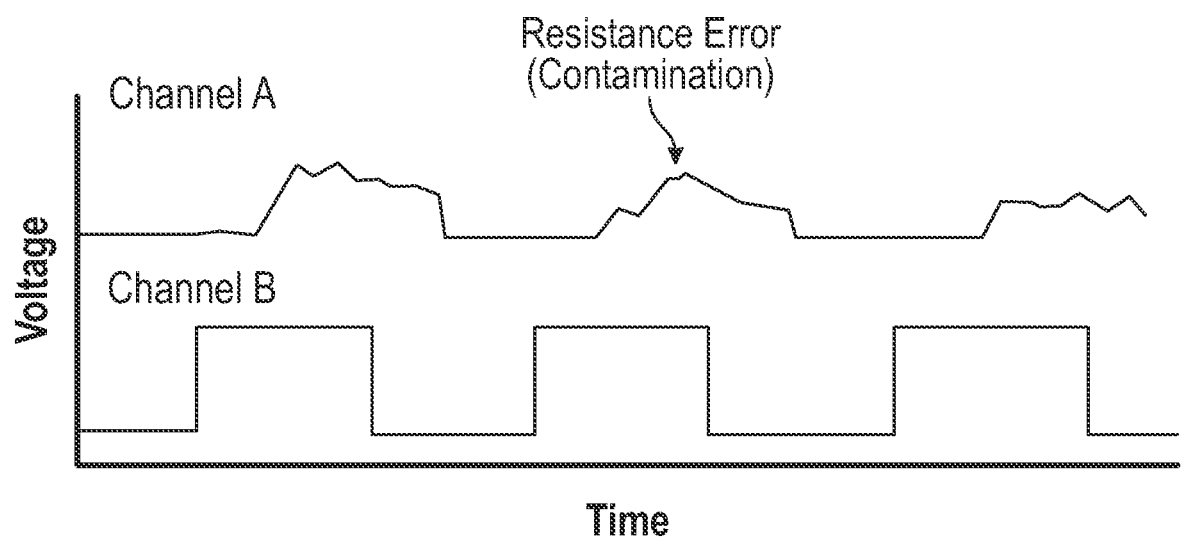

Resistance: The algorithm can be used to analyze resistance of the encoder signal to identify noise in the encoder. An analog voltage measurement of the input lines can give a rough measure of resistance in the encoder circuit. Resistance should either be very low when connected, or very high when disconnected. If an abnormal resistance between the normal values is observed, e.g., determined by an instability of an output signal of an encoder channel, this can be indicative of dirty or corroded contacts, contamination, or ingress of a conductive liquid such as water or insulin. FIG. 2E shows two example voltage-time plots featuring resistance errors indicative of noise on one of the channels (channel A) of an example encoder. The algorithm can process the voltage output of each channel and determine whether, for any point in time of the signal, the voltage is within a particular 'high' range or 'low' range or is changing at a particular rate of change not associated with a proper rise or fall of the signal between states. For example, the algorithm can monitor a voltage of an encoder channel output to determine a stability of the voltage within a predetermined stability threshold of supply voltage or a ground voltage. For example, the threshold can be a value or range based on empirical or precomputed data values. Some examples of the predetermined threshold of stability include, but are not limited to, within 10%, 5% or 1% of the supply voltage or ground.

Example Embodiments of Multi-Channel Pattern Encoders

Figure 3A:
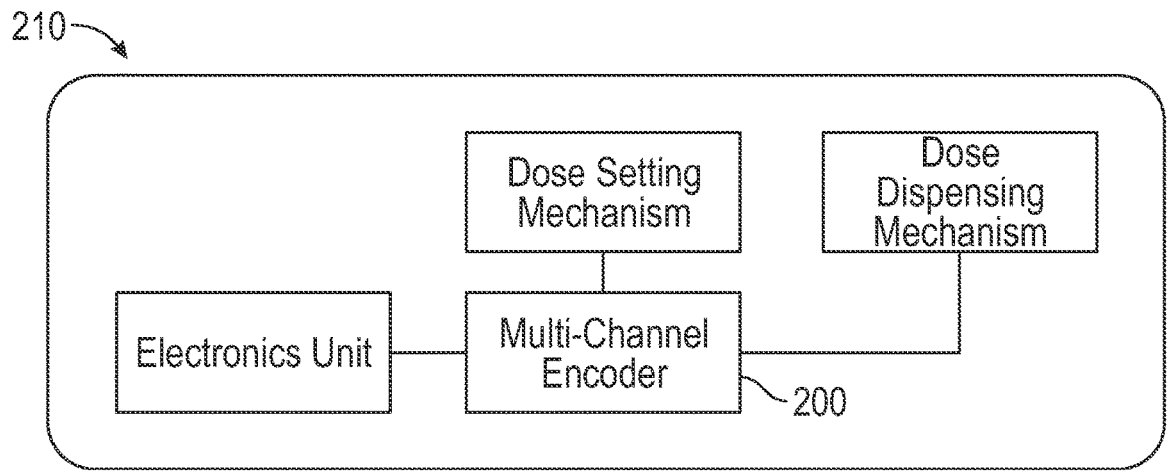
FIG. 3A shows a block diagram of a pen device including an example embodiment of a multi-channel pattern encoder in accordance with the present technology.

FIG. 3A shows a block diagram of an example embodiment of the pen device 10, labeled pen device 210, which includes an example multi-channel pattern encoder 200 in accordance with various embodiments of the present technology. The multi-channel pattern encoder 200 is in communication with the dose setting mechanism and/or the dose dispensing mechanism to quantify positional changes (e.g., rotations) of the mechanism and generate output signals. The multi-channel pattern encoder 200 is in communication with the electronics unit of the pen device 210 to provide the output signals of the encoder 200 to the electronics unit. In some implementations, the electronics unit (e.g., processor) of the pen device 210 can process the output signals in accordance with the disclosed methods herein for detecting and reporting fault conditions of the pen device 210; whereas, additionally or alternatively, in some implementations the electronics unit of the pen device 210 transmits the output signals to the companion device 5 such that the data processing unit of the companion device 5 processes the output signals in accordance with the disclosed methods herein for detecting and reporting fault conditions of the pen device 210.

Three-Channel Pattern Encoder Embodiments

Figures 3B, 3C:
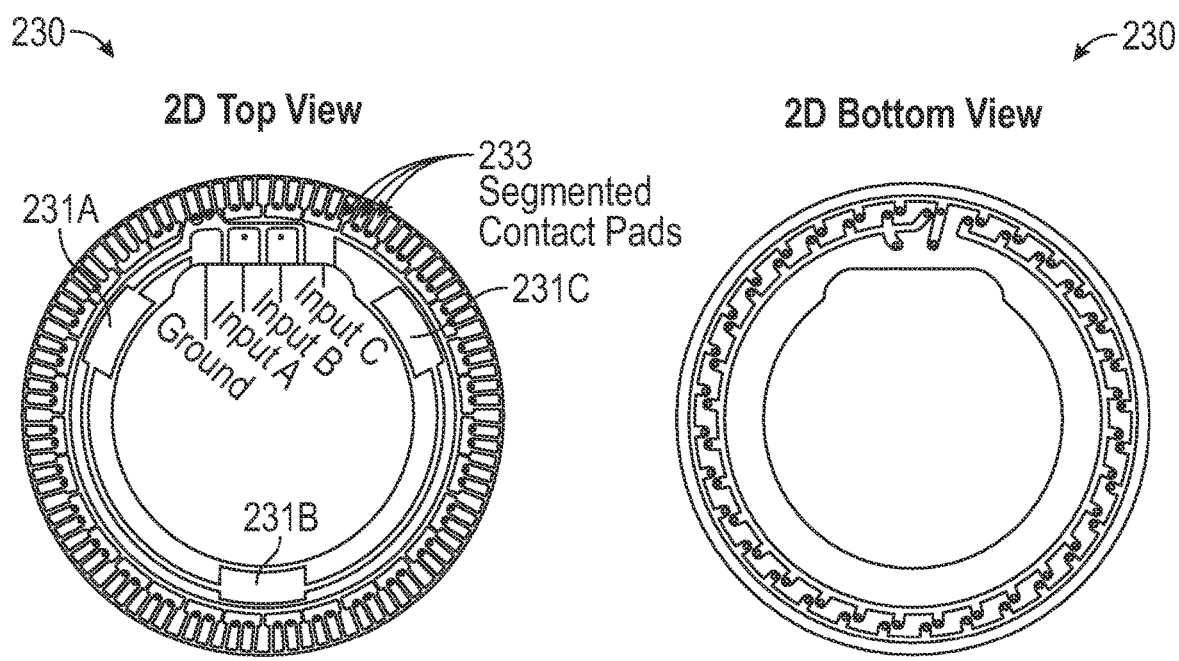
FIGS. 3B-3D show illustrative diagrams of an example embodiment of a pattern wheel of a multi-channel pattern encoder in accordance with the present technology.
Figure 3D:
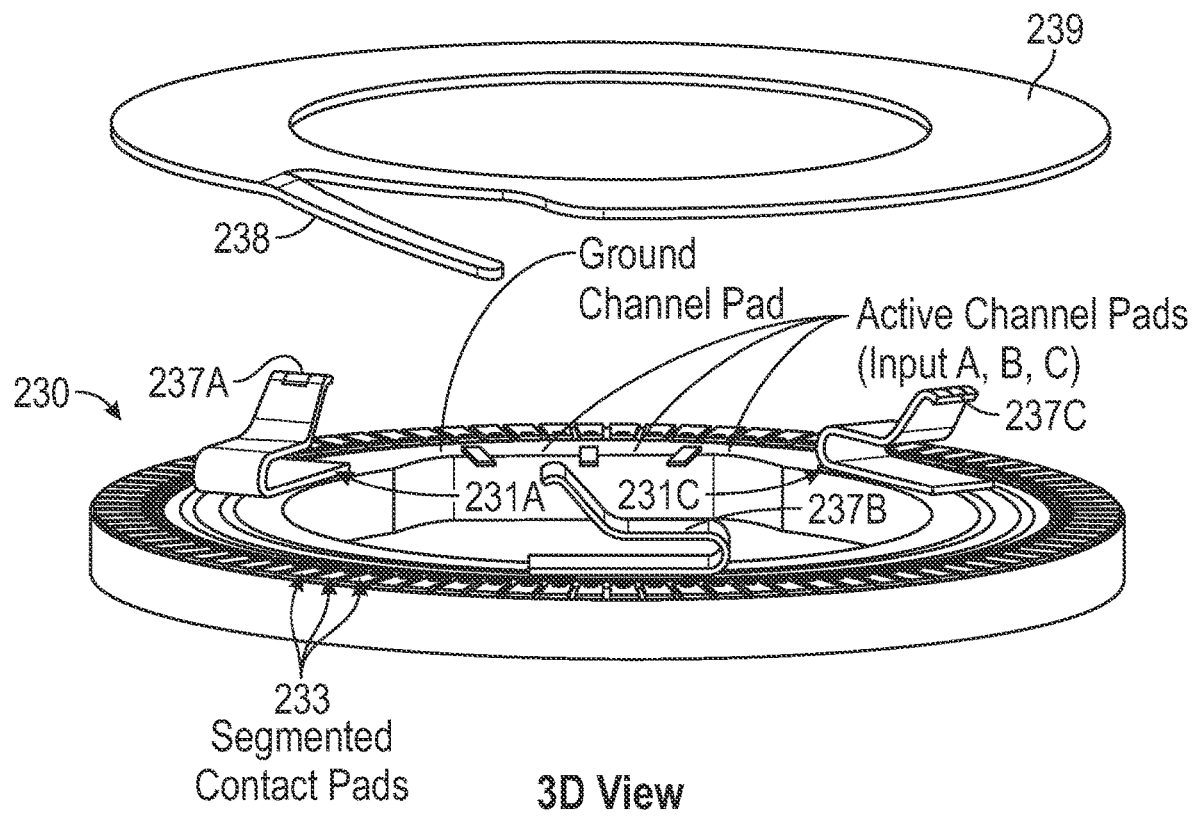
Figure 3D:
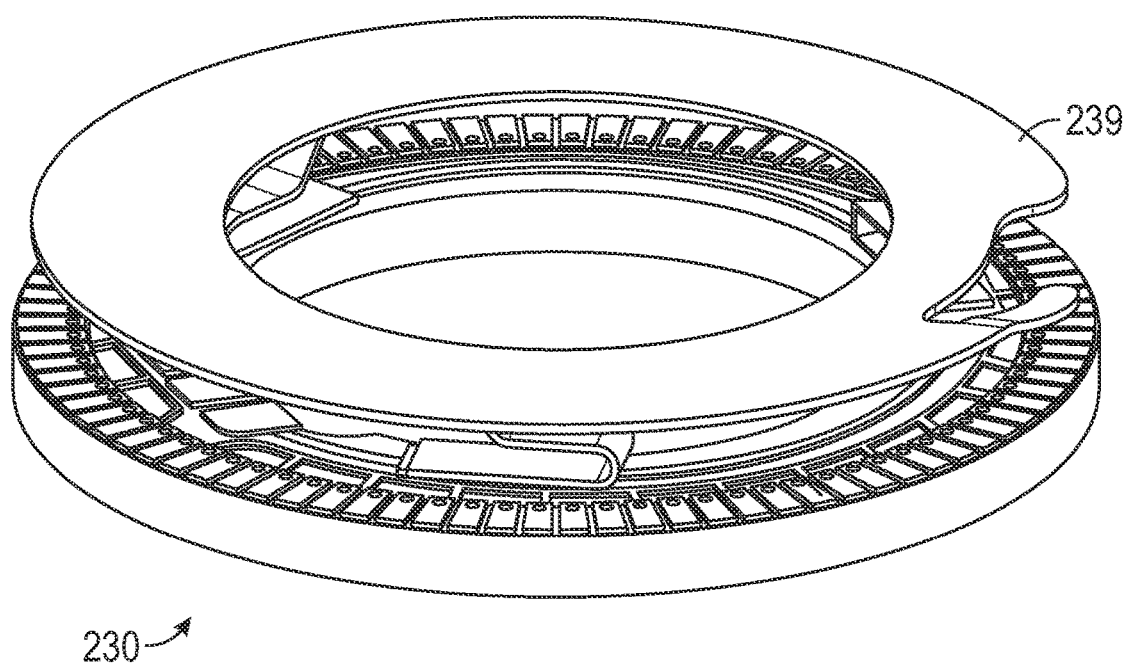

FIGS. 3B-3D show illustrative diagrams of an example embodiment of a pattern wheel of the multi-channel pattern encoder 200, labeled as encoder pattern wheel 230, which includes three active channel pads (e.g., labeled "Input A", "Input B", "Input C") with the conductive pattern of the pattern wheel for measuring three inputs, respectively, and which includes a ground channel pad and ground line formed on the pattern wheel 230. The example pattern wheel 230 can be coupled to the dose setting mechanism and/or the dose dispensing mechanism of the pen device 210.

FIG. 3B shows a 2D top side view and FIG. 3D shows a 3D top side view of the example encoder pattern wheel 230 depicting a pattern of the three channels, also referred to as "inputs", and ground on the surface of the pattern wheel, e.g., which can be configured on a printed circuit board. The three channels correspond to the three active channel pads (Input A, B and C) of the encoder pattern wheel 230 shown in FIGS. 3B and 3D; and the ground on the surface of the pattern wheel corresponds to the ground channel pad of the encoder pattern wheel 230 shown in FIGS. 3B and 3D. The encoder pattern wheel 230 includes an array of segmented contact pads 233, each corresponding to one of the three inputs, arranged around the outer periphery of the pattern wheel. The segmented contact pads 233 interface with a sweeping contact 238 (e.g., spring-loaded contact), shown in FIG. 3D, that sweeps around the pattern wheel 230 to contact the individual contact pads as rotation occurs. Each of the segmented contact pads 233 provides an electrically conductive area to electrically interface with the sweeping contact 238. As shown in the diagram of FIG. 3B, the example encoder pattern wheel 230 includes three large ground pads 231A, 231B, 231C around the inner periphery, of which, can make ground connections to a single rotating contact piece 239 via the spring connectors 237A, 237B, 237C, respectively (shown in FIG. 3D). Notably, in other examples, the single rotating contact piece 239 can contact the ground channel by other connection or connections than the one or more spring connectors 237. Of the three channel inputs, one of the inputs (labeled "Input C" in FIG. 3B) is connected to every third segment in the pattern of segmented contact pads 233 surrounding the peripheral (outside) of the encoder pattern wheel 230. In some embodiments, the pattern of segmented contact pads 233 is disposed on the inner peripheral region of the encoder pattern wheel 230, and the channel pads (e.g., the ground pad, the three example channel input pads, and large contact pads 231A-C) are arranged on the outer peripheral region of the encoder pattern wheel 230.

FIG. 3C shows the underside view of the example pattern wheel 230 of FIG. 3B, illustrating one method for routing the electrical circuits. FIG. 3D shows three dimensional views of the example pattern wheel 230. For example, the three example inner ground pads 231A, 231B, and 231C are configured to provide a mounting surface to which a corresponding conductive spring connector 237A, 237B, 237C, respectively, contacts upon to electrically couple to the single rotating contact piece 239. In this example, the ground pads are provided for mechanical stability, and, in some embodiments, could be configured as a single ground pad or two or more ground pads, or no pads whereby a connection between ground of the pattern wheel 230 and the single rotating contact piece 239 is established. In some embodiments, for example, the single rotating contact piece 239 includes a solid inner ring that the conductive spring connectors contact, and the spring-loaded sweeping contact 238 that sweeps across the segmented contact pads 233 of the pattern wheel 230.

Figure 3E:
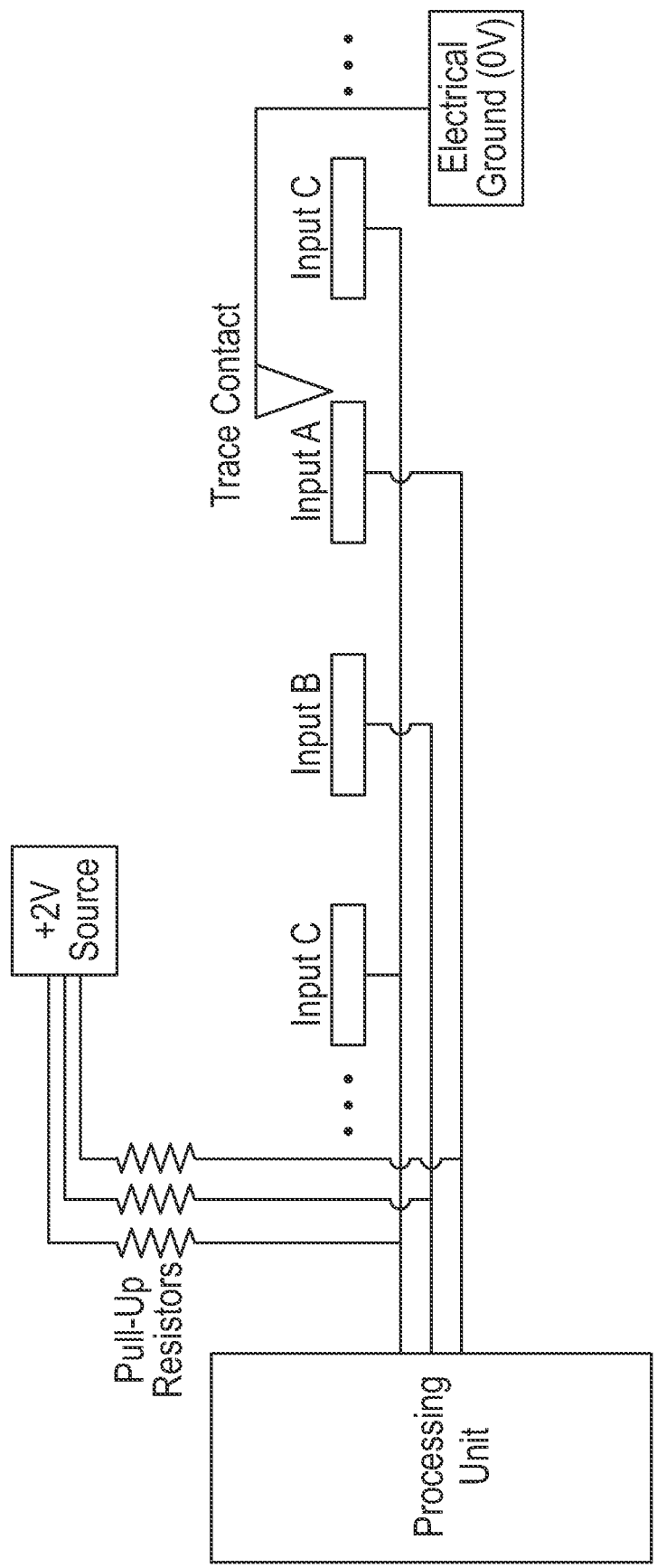
FIG. 3E shows a diagram of an example embodiment of the multi-channel pattern encoder including the pattern wheel of FIGS. 3B and 3C in an example implementation.

FIG. 3E shows a diagram of an example implementation of the multi-channel pattern encoder 200, such as the encoder pattern wheel 230. As shown in the diagram of FIG. 3E, the example encoder 200 is configured to have each electrical contact connected to an input line of the processing unit, which can read the voltage of the inputs, e.g., input A, input B, input C. In some embodiments, the encoder 200 is configured to have the processing unit read the input lines digitally, e.g., detecting whether the input signals are above or below a certain threshold and reporting a "0" or "1" as an output. In some embodiments, the encoder 200 is configured to have the processing unit read the analog voltage on the input lines, e.g., in which these signals are still converted to a digital value at the processing unit, internally; but rather than reporting a "0" or "1", the output reported by the processing unit may range from 0 to 255 or 0 to 65535, for example, representing the relative voltage level detected.

As shown in the diagram of FIG. 3E, the example active pattern encoder includes a plurality of encoder segments connected to the three inputs A, B and C in repeating order, e.g., . . . C B A C B A C B A C B A . . . etc. Mechanically, the example multi-channel pattern encoder 200 (e.g., such as the encoder pattern wheel 230) operates by sensing relative motion between the trace contact(s) and the pattern contact pads. For example, the trace contact(s) may rotate with the dispensing mechanism, and the pattern contact pads are fixed on the pattern wheel, which may be fixed and not rotate; or, vice versa, the pattern wheel having the fixed pattern contact pads may rotate and the trace contact(s) may be fixed rotationally. In some implementations, for example, the pattern wheel and the trace contact(s) can rotate, where the relative motion is detected.

Multi-Channel Sequential Pattern Encoder Embodiments for Intrinsic Fault Detection In another example embodiment of a multi-channel encoder in accordance with the present technology, e.g., the encoder includes a three (or more) channel encoder that can traverse a pattern in such a way that there is always at least one contact disconnected, and always at least one contact connected. An example sequence for clockwise rotation may be: [001], [011], [010], [110], [100], [101], [001], etc. In this way, the states [000] and [111] are invalid, indicating an open circuit (e.g., connection fault) or a short circuit (e.g., liquid ingress). As such, the example multi-channel pattern encoder is capable of detecting intrinsic faults in the interfaced device, e.g., such as the pen device 10.

Figure 4A:
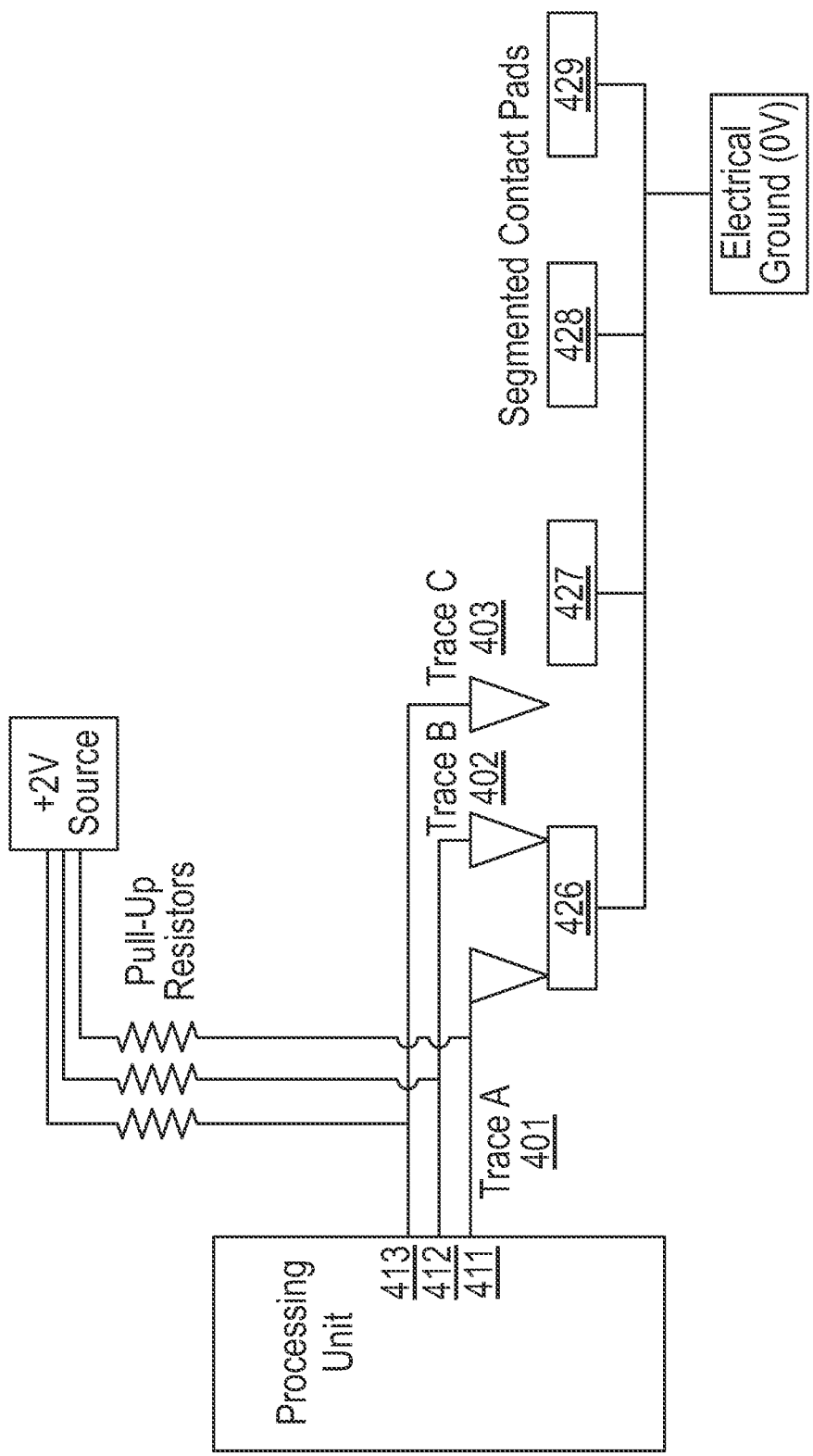
FIG. 4A shows a diagram of an example embodiment of a multi-channel pattern encoder in accordance with the present technology.

FIG. 4A shows a diagram of an example embodiment of a multi-channel pattern encoder in accordance with the present technology. In this example, the multi-channel pattern encoder includes three trace contacts 401, 402 and 403 (corresponding to trace contacts A, B, C, respectively) that are connected to the three inputs (channels) 411, 412, 413 interfaced to the processing unit, in which all three trace contacts sweep across a pattern of segments of the encoder's pattern wheel that are all grounded. In an example implementation of the encoder shown in FIG. 4A, at least one of trace contact A, B or C is not in contact with any one of the segmented contacts on the panel wheel that is grounded; i.e., at least one trace contact is disconnected with ground. In the example illustrated in FIG. 4A, trace contact C is not in electrical contact with ground. Also, at least one of trace contact A, B or C is in contact with a segmented contact, and thereby is always connected with ground. In this three-channel example, there would never be more than two trace contacts not in contact with ground as the three trace contacts sweep across the segmented contact pads 426, 427, 428, 429, etc. of the encoder under normal operation. If the encoder is operating properly, then one input should always detect a signal (i.e., output is [1] or analog equivalent) and one channel should detect ground (i.e., output is [0] or analog equivalent). If it does not, then the encoder indicates damage, contamination, corrosion, or some other connection problem.

Figure 4B:
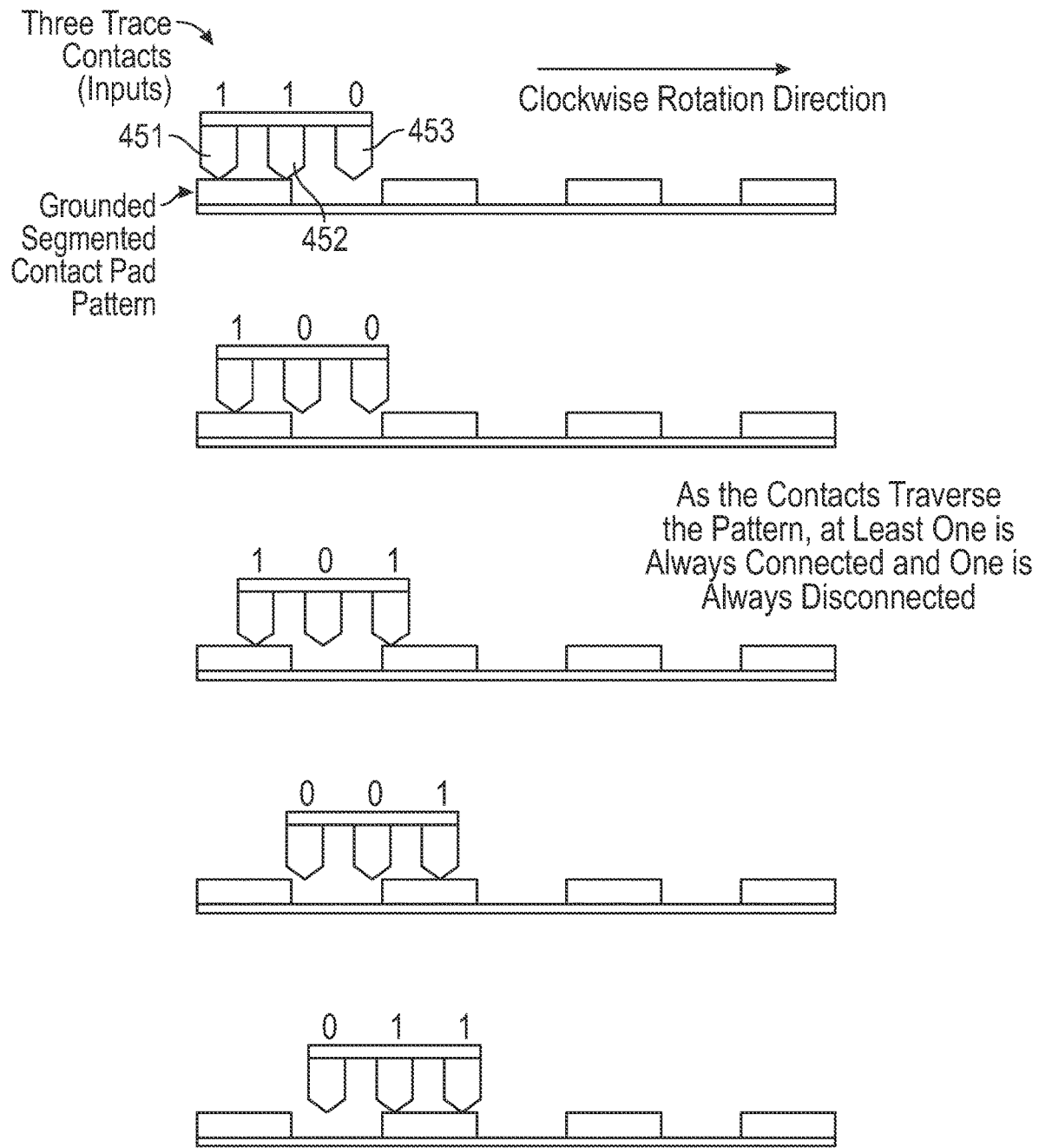
FIG. 4B shows a diagram of an implementation of an example embodiment of the multi-channel encoder of FIG. 4A.

FIG. 4B shows a diagram of an implementation of an example embodiment of a three-channel pattern encoder, like that shown in FIG. 4A, in accordance with certain embodiments of the encoder 200. As shown in the diagram of FIG. 4B, one contact among the first trace contact 451, second trace contact 452 or third trace contact 453 of the encoder is always disconnected with ground, and one contact associated with the first, second or third trace contacts of the encoder is always connected with ground. For example, the diagram depicts a sequence for a clockwise rotation in which the encoder detects [110], [100], [101], [001], and [011], e.g., valid states indicating no faults with the pen device 210.

Multi-Channel Sequential Pattern Encoder Embodiments for Explicit Fault Detection In some implementations of an intelligent medicine administering system 100 including the example multi-channel pattern encoder 200 or other example embodiments of a multi-channel encoder in accordance with the present technology, the system is configured to provide explicit fault detection capabilities based on operations of the encoder, e.g., for liquid detection and ground sensing.

Liquid detection: The system 100 can detect explicit faults in a medicament delivery device based on the presence of liquid in the device. For example, the encoder of the pen device, such as the encoder 200 of the pen device 210, can be configured such that, with an encoder pattern connected to ground and the two active contacts pulled high (e.g., connected to a 1.5 volt source through 500 k-ohm resistors), the third input line is pulled high. As such, the third line could be exposed near the active contacts but not directly contacting any other components, such that any conductive liquid (such as tap water or insulin) entering the encoder would bridge the liquid detection contact and the pattern wheel. This would then be detected as a voltage drop of the liquid detection input, and indicative of a fault with the pen device 210.

Figure 4C:
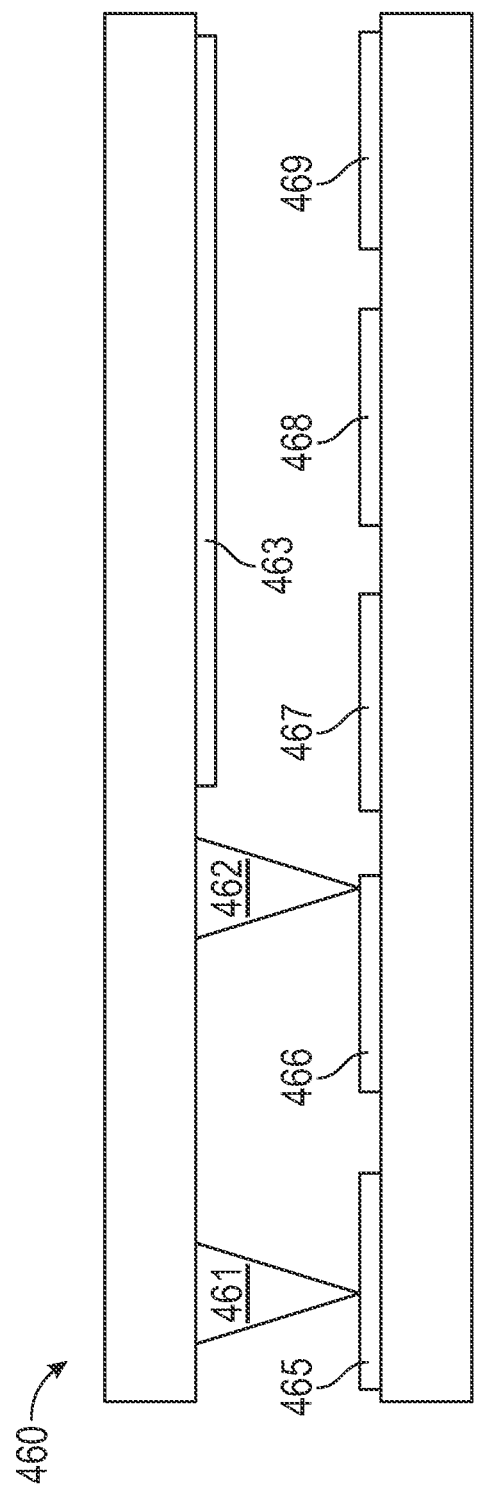
FIG. 4C shows a diagram of an example embodiment of the multi-channel pattern encoder operable to detect explicit liquid faults in a medicament delivery device.

FIG. 4C shows a diagram of an example embodiment of a multi-channel pattern encoder 460, in accordance with certain embodiments of the encoder 200, that is operable to detect explicit liquid faults in a various devices such as a medicament delivery device. As shown in the diagram, the multi-channel pattern encoder 460 includes a pattern contact pads 465, 466, 467, 468, 469, etc. on the bottom portion of the encoder; and on the top portion, the encoder 460 includes two sweeping contacts 461, 462 that are touching the pattern contact pads, and a third contact area 463 that touches nothing. However, if liquid floods the area, the third contact area 463 will make some electrical contact with the pattern contact pads and register a signal, indicating an explicit fault.

Ground sensing: For conventional mechanical encoders, typically a rotary encoder pattern consists of a solid inner conductive ring used for connection to ground, and segmented conductive areas around the ring, used for rotational measurement. A sweeping electrical contact contacts the solid ring to hold the pattern at ground, while active contacts trace across the conductive segments. By adding another contact on the solid ring, set as an input, this contact can be used to constantly detect the ground connection. This input should always detect ground, and if it does not then that indicates damage, contamination, corrosion, or some other connection problem.

In some embodiments of the multi-channel encoder, the encoder includes a ground sensing contact that is operable as an input with respect to the encoder. Yet, during an active dose setting and/or dispensing event in which the encoder is operated, for example, while edge transitions are being detected by the active channels, the ground sensing contact channel may be set as a ground output. In this way, the ground ring will have redundant ground connections, helping ensure clean signal quality. Then when the dose is complete, the contact can be set to an input again to monitor proper ground connection.

Figure 4D:
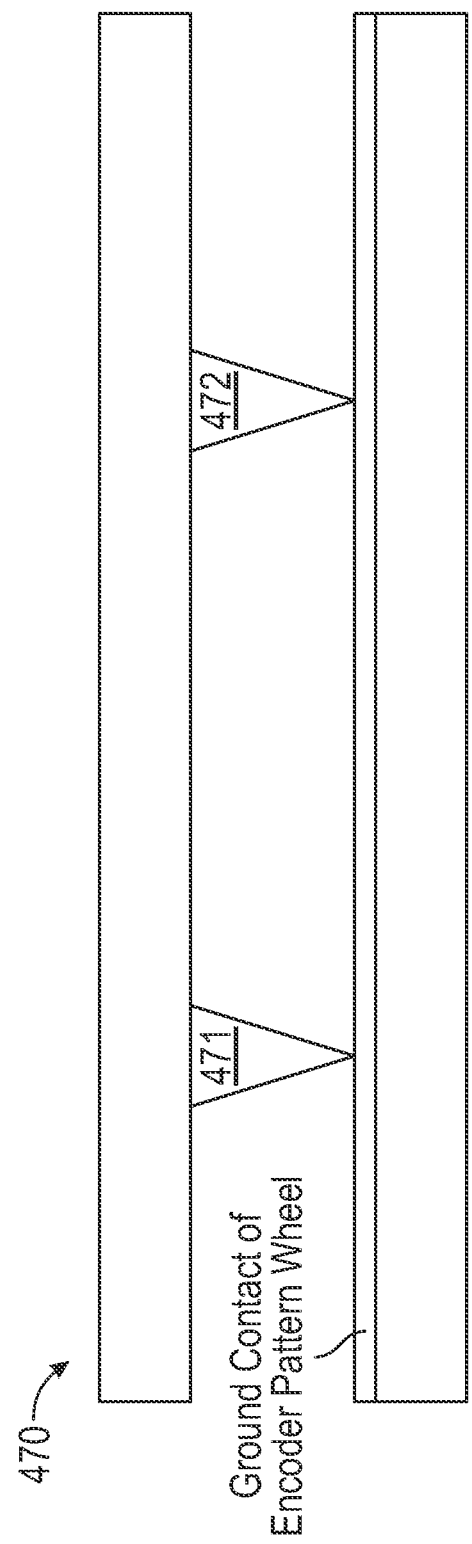
FIG. 4D shows a diagram of an example embodiment of the multi-channel pattern encoder operable to sense ground for detection of explicit faults in a medicament delivery device.

FIG. 4D shows a diagram of an example embodiment of the multi-channel pattern encoder 470, in accordance with certain embodiments of the encoder 200, that is operable to sense ground for detection of explicit faults in a medicament delivery device. Notably, the diagram of FIG. 4D only shows the ground connections on the solid ring, and the A and B channel contacts are not pictured. For example, one of these contacts would be the ground connection, and the other would be an input measuring voltage. As illustrated in FIG. 4D, the 'ground' contact of the example ground-sensing multi-channel pattern encoder 470 is typically in contact and will detect 0V or ground. However, if something were damaged or corroded, the ground-sensing encoder would not make contact and would detect a fault.

Multi-Channel Sequential Pattern Encoder Embodiments for Intrinsic Detection with Quadrature Encoder In some implementations of the intelligent medicine administering system 100 including the example including the example encoder output processing module 152, the system is configured to provide intrinsic fault detection capabilities based on data processing the outputs of an encoder, e.g., including the disclosed multi-channel pattern encoders and a conventional quadrature encoder.

Pattern Resistance: The quadrature encoder includes a solid conductive ring that forms the encoder pattern when the ring is a material with a moderate resistivity, or the encoder includes a fixed resistor between the ground connection ring and the segmented pattern. For example, with a moderate resistivity, or the fixed resistor configuration, any time an input line contacts the pattern, it should read a specific resistance (or voltage level) indicating that current is flowing only through the pattern. If the resistance is lower than expected, then that indicates a contaminate such as water also carrying some current, lowering the overall resistance in the circuit.

Resistance in Pattern Gaps: For conventional encoders, typically there is a dielectric (such as plastic or soldermask) between the conductive segments of the encoder pattern. Instead, if this material is slightly conductive (with high resistance) and in contact with ground, or if it is conductive (with low internal resistance) and connected to ground via a large value resistor, then it can help detect damage. Whereas a conventional quadrature encoder would either be completely connected or completely disconnected, the example embodiments of the encoder 200 can include material with a moderate resistivity and/or a fixed resistor coupled between the inner conductive ground ring and the segmented pattern to provide inputs that should never be completely disconnected from ground. They should only alternate between sections of high and low resistance. In this way, if they are ever completely disconnected, this indicates damage to the encoder, circuitry or other components of the device, e.g., pen device 10.

In some implementations of these example embodiments of the encoder 200, the encoder can be read (e.g., by the electronics unit) by continually monitoring analog voltage of the inputs and evaluating it as it rises and falls.

Yet, in some implementations of these example embodiments of the encoder 200, a simpler and faster method than continuous analog measurement (e.g., continually monitoring analog voltage of the inputs) is to only measure analog voltage when the encoder is at rest. For example, once motion is detected, the input can be switched to a digital mode. If the pattern resistance is sufficiently low and the gap resistance is sufficiently high, a digital input can still correctly interpret the encoder signal. Then when it returns to rest, the analog voltage can again be sampled to ensure proper connections.

Figure 5A:
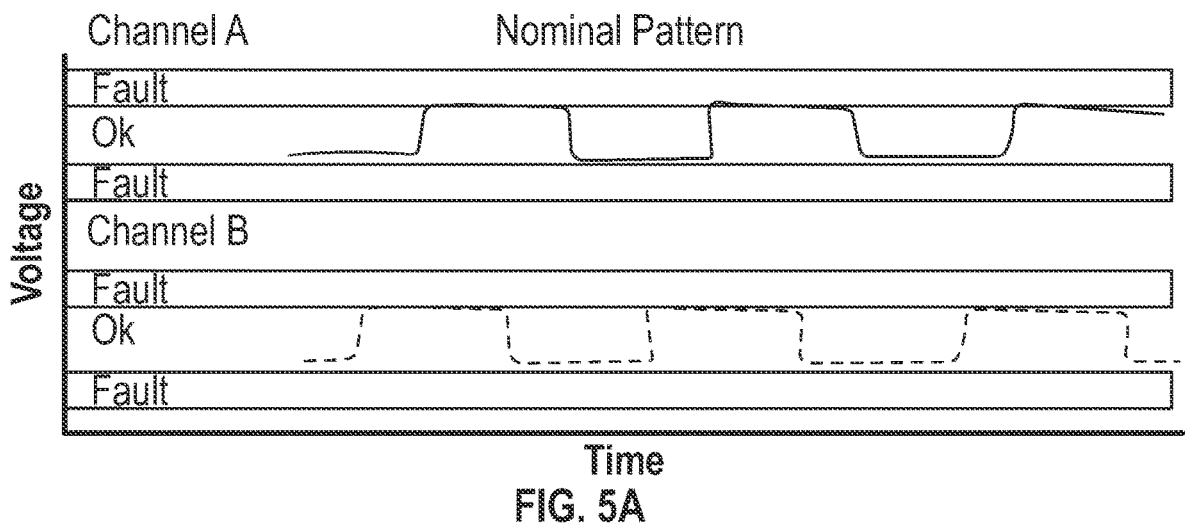
FIG. 5A-5C show example data plots of implementations of example encoder signal analysis schemes in accordance with the present technology.
Figure 5B:
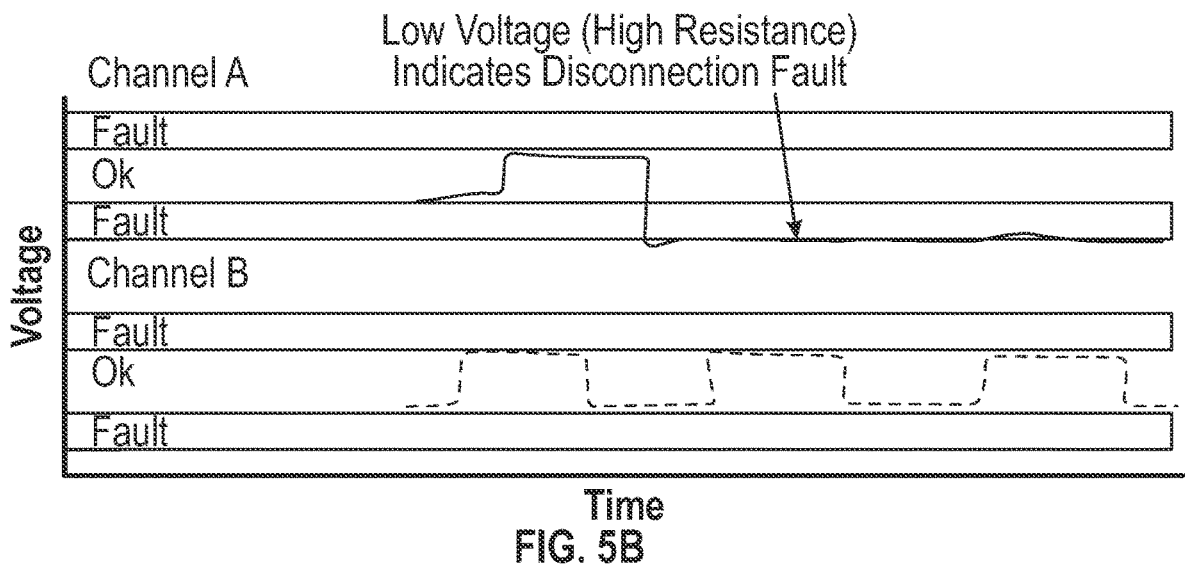
Figure 5C:
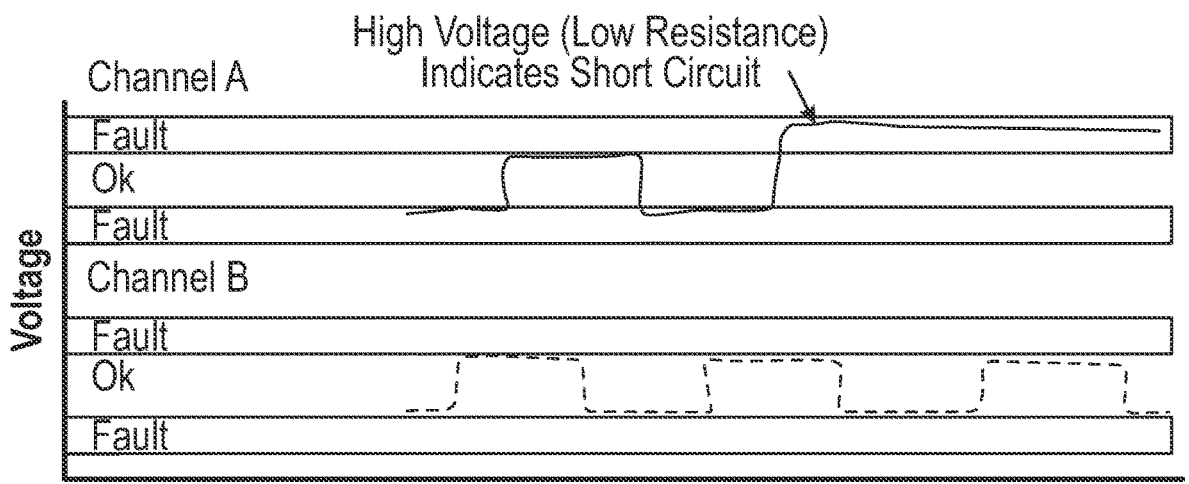

FIG. 5A-5C show example data plots of encoders implementing these example features. If the voltage ever reaches ground or full input voltage, that indicates a fault. For example, if the circuit operates at 2 V, the valid input range may be from 0.2 V to 1.8 V, and anything below 0.2 V indicates a connection fault and anything above 1.8V indicates a short circuit. FIG. 5A shows an example where the two quadrature encoder channels A and B are operating within valid input range. FIG. 5B shows an example where the quadrature encoder channel A has an input signal below the minimum range value (e.g., <0.2 V), which can indicate a disconnection fault. FIG. 5C shows an example where the quadrature encoder channel A exceeds the maximum range value (e.g., >1.8 V), which can indicate a short circuit.

Example Embodiments and Implementations of Fault Direction Using an Encoder with a Single Trace Contact and a Multi-Channel Active Pattern For example, some encoders have multiple input contacts that sweep across conductive stripes on a grounded pattern. One requirement of this approach is that the alignment between contacts is critical to ensure proper pattern sequencing. In some instances, the contacts may be spring-loaded and flexible, which can create challenges in ensuring the required alignment between contacts, especially for high resolution encoders.

As shown in FIGS. 3B-3E, an example of the multi-channel encoder 200 is includes a pattern wheel 230 including a solid conductive ring coupled to the dose setting mechanism and/or dose dispensing mechanism, in which the conductive ring includes an active pattern produced with accurate fixed-location contact pads, and a single grounded trace contact with non-critical alignment that can be swept along the active pattern to indicate movement. The pattern is referred to as "active" because its contact pads are connected to pull-up resistors and processor inputs. For example, with minimal gaps between the contact pads on the pattern wheel 230, it can be ensured that the contact is always contacting at least one channel, but it is not wide enough to bridge all three. As such, the states [000] and [111] are fault conditions.

Figure 6:
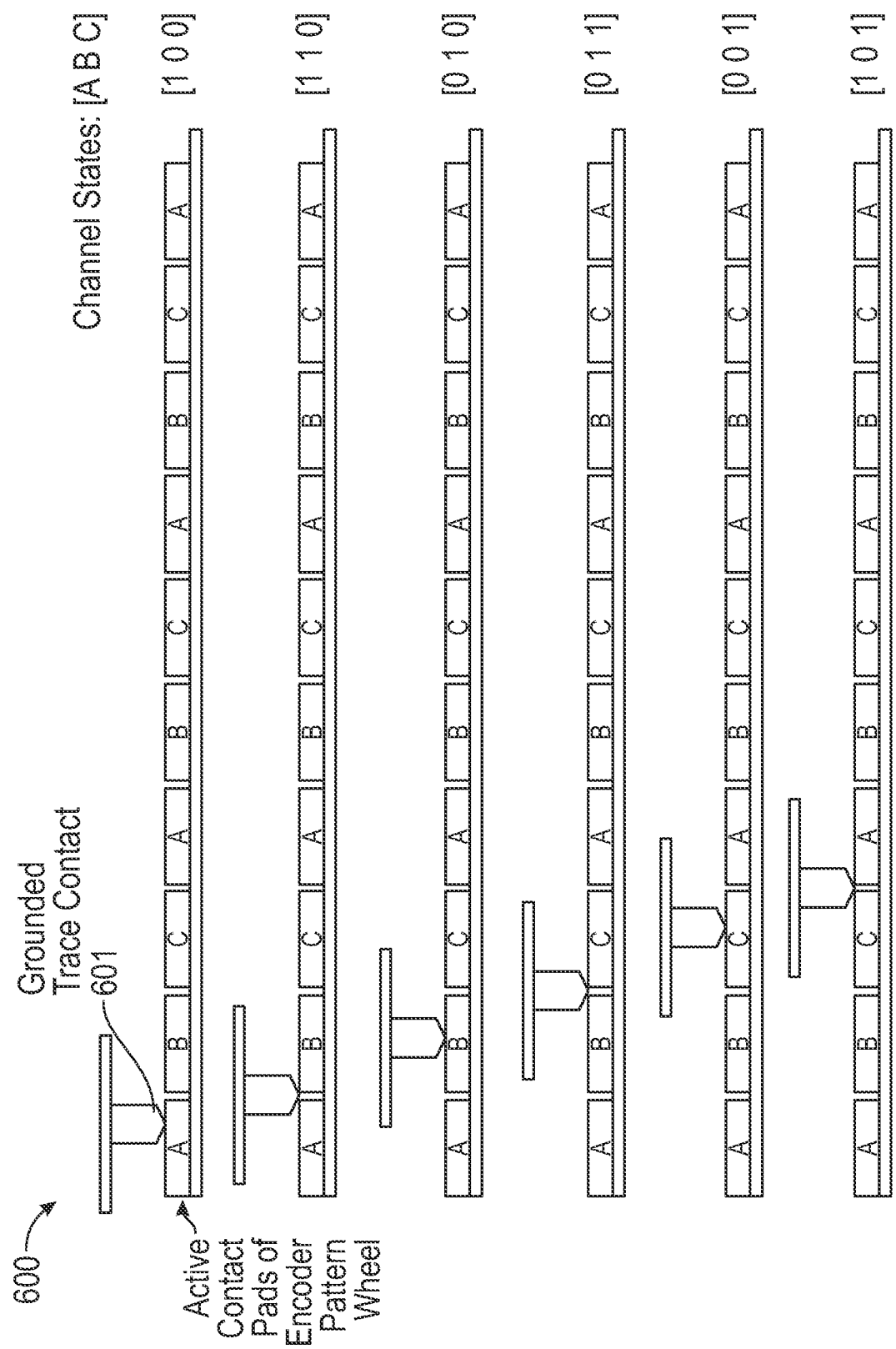
FIG. 6 shows a diagram of an example monitoring implementation of an example multi-channel active pattern encoder in accordance with the present technology, in which no fault is correctly detected.

FIG. 6 shows a diagram of a monitoring implementation using an example embodiment of the multi-channel active pattern encoder 600 in accordance with the example embodiment of the pattern wheel 230 shown in FIGS. 3B-3D. In this embodiment shown in the diagram of FIG. 6, the segmented contact pads are associated with channels or inputs A, B, and C and are electrically "active." The single trace contact 601 is grounded and is operable to make contact with the segmented contact pads as the trace contact 601, the active contact pads, or both are moved with respect to each other. As shown in the top situation of the diagram, the first active region "A" is in contact with the trace contact 601 such that the output signal of the encoder 200 is [100]. As the single channel transitions, e.g., trace contact 601 rotates around the pattern wheel, when the trace contact 601 is between two active regions, the output signal includes two "1" outputs; for example, the output signal of the encoder 200 is [110] when the single channel transitions between the first and the second active regions "A" and "B", respectively. For example, the diagram of FIG. 6 depicts a sequence for a clockwise rotation in which the encoder detects [100] in the first active region, [110] in transition between the first and second active regions, [010] in the second active region, [011] in transition between the second and third active region, [001] when in the third active region, and [101] when in transition between the third and first active regions, e.g., which are all valid states indicating no faults with the pen device 210.

Figure 7:
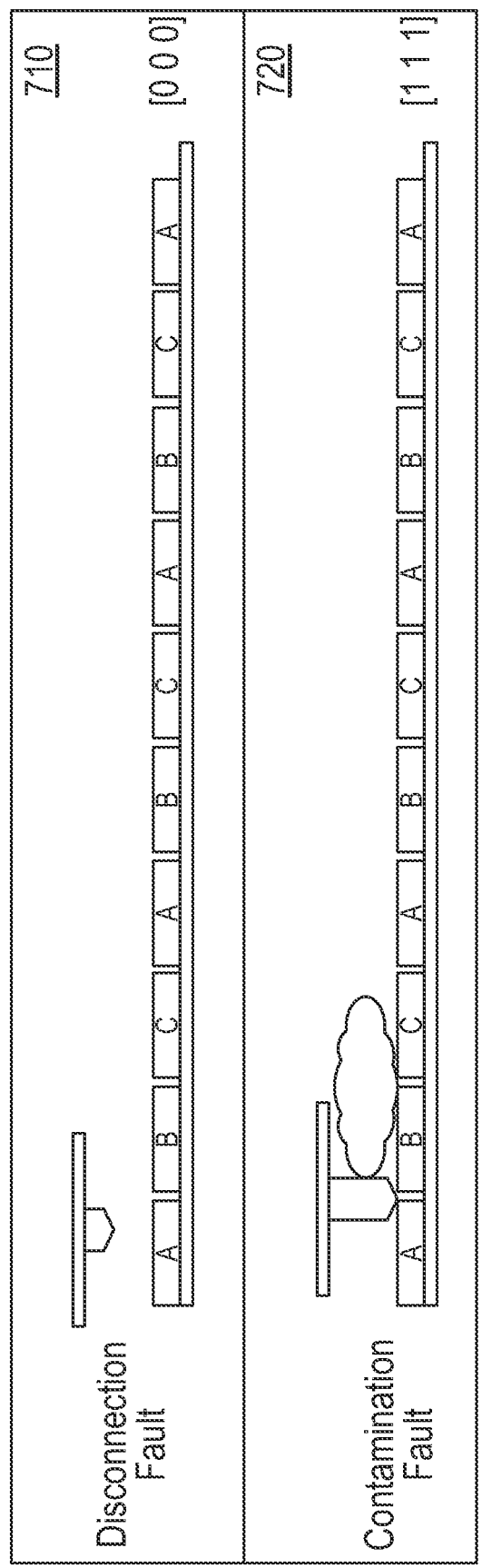
FIG. 7 show a diagram of an example monitoring implementation of an example multi-contact active pattern encoder in accordance with the present technology, in which a fault is correctly detected.

FIG. 7 shows a diagram of monitoring implementations of an example multi-channel active pattern encoder having a single-trace and including the pattern wheel 230 in which a fault is correctly detected. By example, the implementations illustrated in FIG. 7 can employ the encoder 600 shown in FIG. 6. As shown in the top illustration 710 of FIG. 7, the single trace contact is not in contact with any of the active regions, such that the output signal of the encoder is [000]; and in the bottom illustration 720 of FIG. 7, the single contact is in contact with an active region and a substance (e.g., water ingress) which is across two other active regions, such that the output signal of the encoder is [111].

Additional advantages of such embodiments of the encoder include, for example, opportunities for saving energy by de-powering unnecessary channels and preventing quiescent current draw through them.

Nominally this example encoder 600 produces the pattern [100] [110] [010] [011] etc. However, contacting two channels at once may only be instantaneous as the contact transitions from one pad to the next, so in practice it would be useful to simply monitor for the triggering of the next expected channel and disregard when the previous channel is disconnected, since those will both happen nearly instantaneously.

For example, from initial state [100] the state [110] indicates that channel B has now been connected, but the next state [010] when channel A (first active region) disconnects is not considered significant, as it will happen almost immediately anyway. In the state [100] the only important channel to monitor is B, and possibly C if the system needs to also detect reverse rotation. Once A has been contacted, it is no longer critical to monitor its value. Since A is no longer critical, it can be de-powered to save energy. Its state will be unknown to the system, but this doesn't matter. De-powering can be done instantaneously during rotation, or after a brief timeout period indicating that movement has stopped.

In various embodiments, the system can include a power management algorithm for the example single-trace multi-channel encoder to monitor the state changes, determine what channels are critical to have power supplied, regulate the power to those presently non-critical (e.g., depower non-critical) and those soon-to-be critical (e.g., power a presently depowered channel), and repeating this process continually or intermittently.

Figure 8:
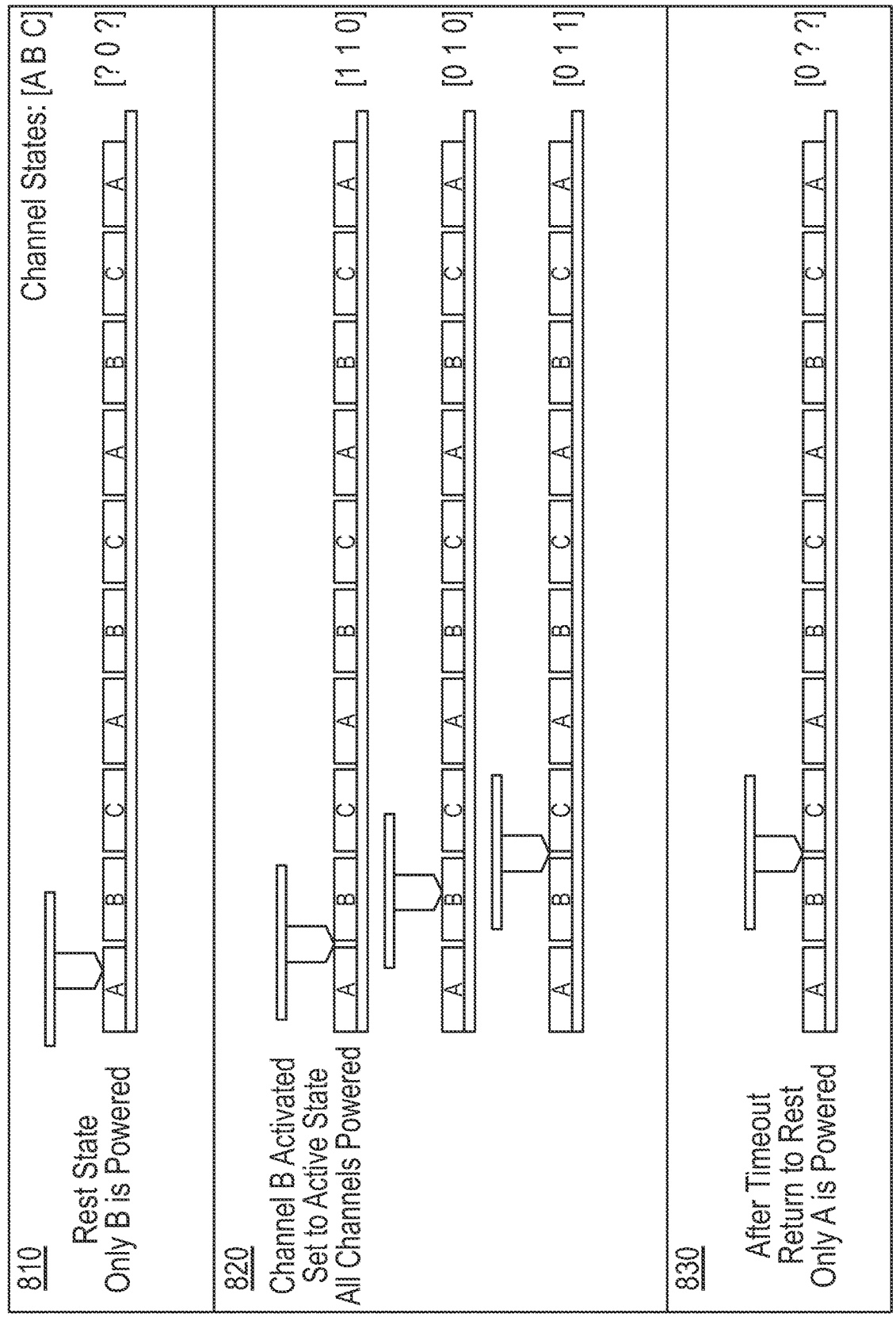
FIG. 8 shows a diagram of a monitoring implementation using an example embodiment of a multi-channel pattern encoder in accordance with the present technology.

FIG. 8 shows a diagram of a monitoring implementation using an example multi-channel active pattern encoder having a single-trace and including the pattern wheel 230. By example, the implementations illustrated in FIG. 8 can employ the encoder 600 shown in FIG. 6. Channels that are powered, and therefore their values can be read by the processor are shown in the 0 or 1 state. Channels that are de-powered, and therefore their values cannot be read by the processor are shown as a question mark "?".

As shown in the top portion of the diagram labeled 810, in the initial position the encoder has previously detected contact with A so it is no longer useful to spend power monitoring that channel, so it is shown as de-powered with a ? state. Similarly, assuming we are not concerned with accurately measuring backward motion, there is no need to power channel C either, as it is known that B will be contacted first, so the state of C is irrelevant. Only channel B is powered, as the processor waits for contact indicating forward movement.

In the subsequent three positions, as shown in the middle portion of the diagram labeled 820, all of the channels are powered during the movement of the single trace so that the processor can measure the magnitude of the movement.

Finally, as shown in the bottom portion of the diagram labeled 830, after no changes in input are registered for some timeout period, the trace contact contacts channels B and C. Because C was the last channel detected, channels B and C are de-powered, preventing energy loss while they remain connected, and only channel A needs to be powered to detect the next forward movement. If a channel is powered while connected, it draws current and uses energy, draining power from the battery or other energy source. If a channel is powered but not connected, it uses a negligible amount of power, so it is energy efficient to power only channels that are disconnected.

Figure 9A:
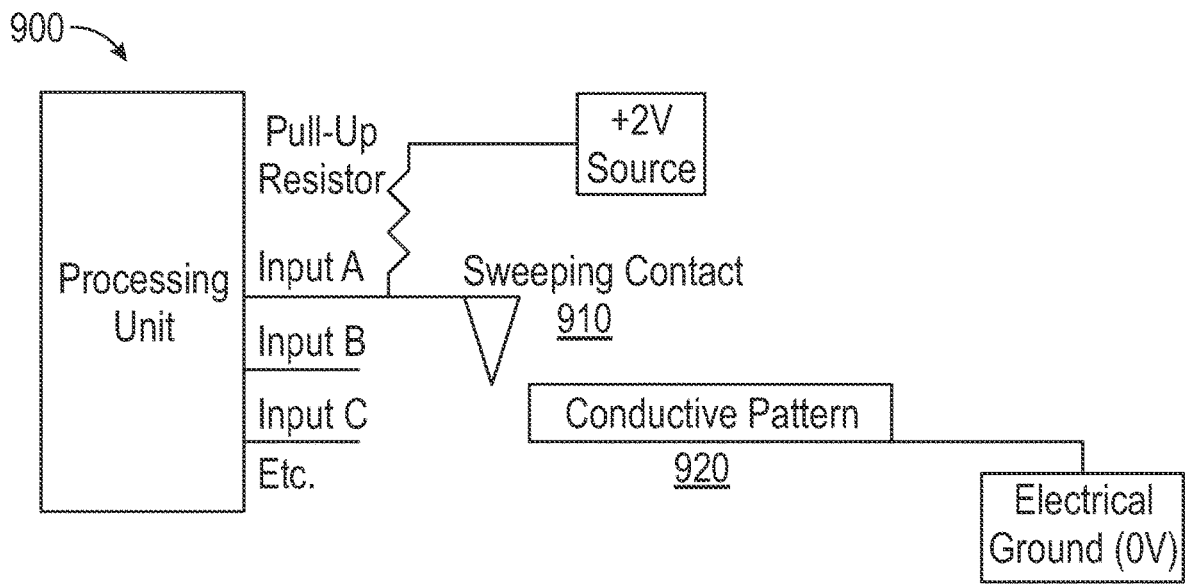
FIGS. 9A and 9B show diagrams of an example embodiment of a multi-channel pattern encoder in accordance with the present technology.
Figure 9B:
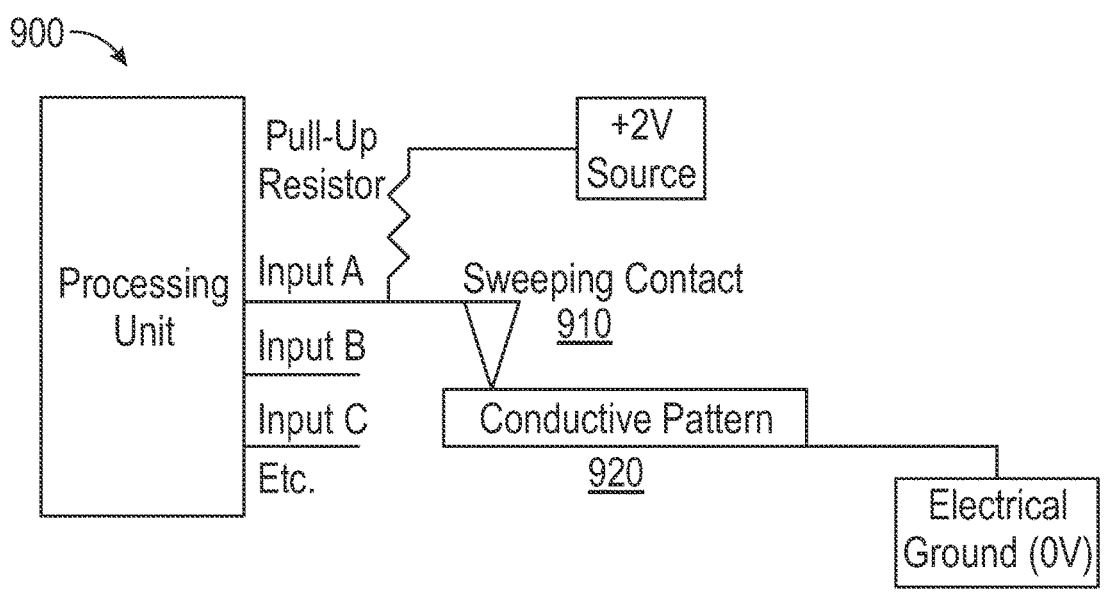

FIGS. 9A and 9B show diagrams of an example embodiment of the multi-channel pattern encoder 900 in accordance with some example embodiments of the encoder 200, showing an electrical schematic for one channel of the multi-channel encoder. In this example, a conductive pattern 920 (e.g., a pattern of segmented contact pads, such as . . . A, B, C, A, B, C, . . . ) is connected to ground, and a sweeping contact 910 (e.g., a spring-loaded sweeping contact) is coupled to a voltage source (e.g., +2V) via a pull-up resistor and is coupled to an input of the processing unit (Input A in this example). When the sweeping contact 910 is not in contact with the conductive pattern 920, as shown in the diagram of FIG. 9A, the detected voltage is 2V at Input A, and there is no current flow. When the sweeping contact 910 is touching a contact pad of the conductive pattern 920, as shown in the diagram of FIG. 9B, the detected voltage is 0V, and there is current flow from the voltage source to ground, through the pull-up resistor. In some embodiments, the encoder 900 can include a single conductive pattern (conductive pattern 920) and multiple sweeping contacts (not shown), where each of the multiple sweeping contacts is connected to a different input of the processing unit (such as Input B and Input C).

Figure 10:
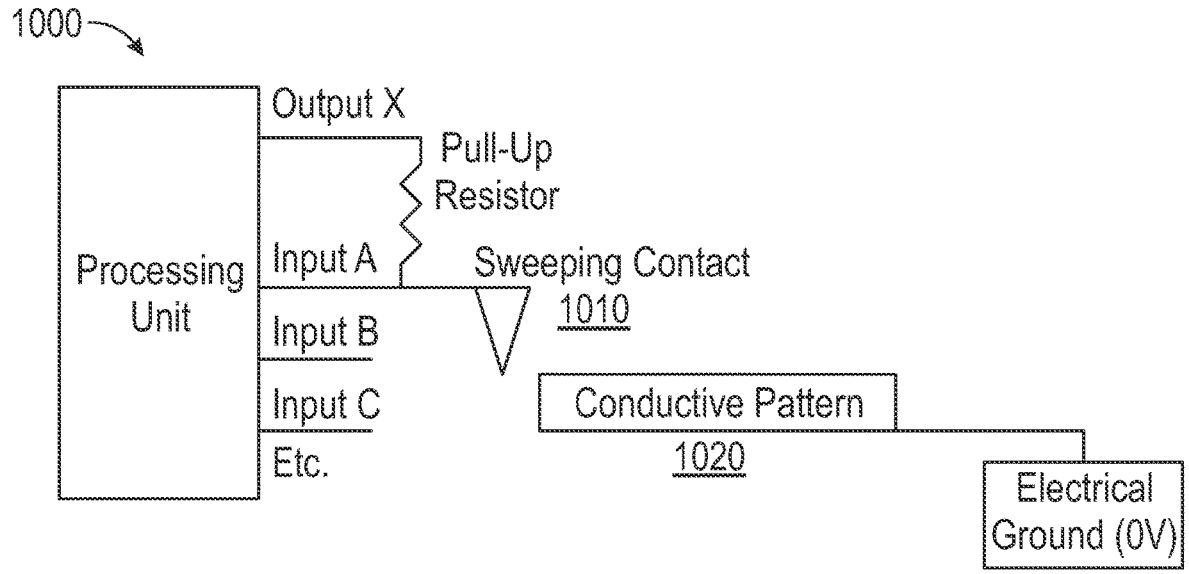
FIG. 10 shows a diagram of an example embodiment of a multi-channel pattern encoder in accordance with the present technology.

FIG. 10 shows a diagram of an example embodiment of a multi-channel pattern encoder 1000 in accordance with some example embodiments of the encoder 200, showing an electrical schematic for one channel of the multi-channel encoder. In this example, a conductive pattern 1020 (e.g., a pattern of segmented contact pads, such as . . . A, B, C, A, B, C, . . . ) is connected to ground, and a sweeping contact 1010 (e.g., a spring-loaded sweeping contact) is coupled to a switchable output of the Processing Unit via a pull-up resistor, as well as coupled to an input of the Processing Unit (Input A in this example). In implementations, for example, to enable the encoder channel, the output is set to a positive voltage (e.g., +2V) and the encoder channel functions similarly to the encoder in FIGS. 9A-9B. However, when the channel is not needed, the output may be disabled, and set to ground (0V) or tristate (disconnected) so that even when the sweeping contact 1010 is touching the conductive pattern 1020, no current is flowing, and therefore no power is consumed by the channel. In some embodiments, the encoder 1000 can include a single conductive pattern (conductive pattern 1020) and multiple sweeping contacts (not shown), where each of the multiple sweeping contacts is connected to a different input of the processing unit (such as Input B and Input C).

Figure 11:
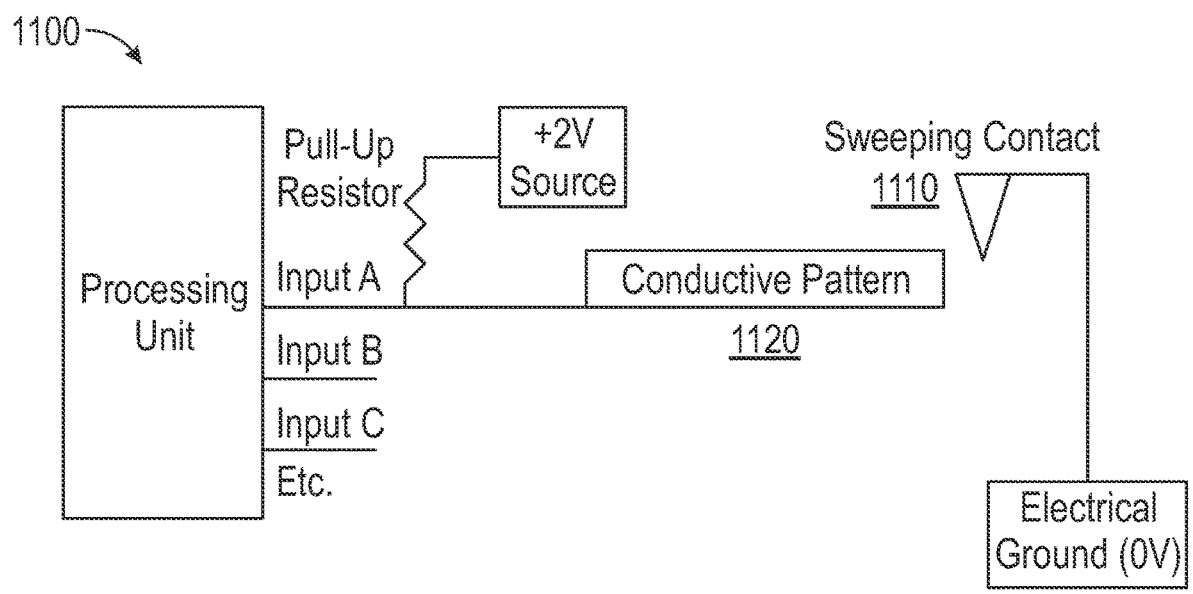
FIG. 11 shows a diagram of an example embodiment of a multi-channel pattern encoder in accordance with the present technology.

FIG. 11 shows a diagram of an example embodiment of a multi-channel pattern encoder 1100 in accordance with some example embodiments of the encoder 200, showing an electrical schematic for one channel of the multi-channel encoder. In this example, elements of a conductive pattern 1120 (e.g., a pattern of segmented contact pads, such as . . . A, B, C, A, B, C, . . . ) are connected to a positive voltage source (e.g., +2V) via a pull-up resistor and are monitored by inputs of the processing unit; a sweeping contact 1110 (e.g., a spring-loaded sweeping contact) is connected to ground. Unlike other example encoders that have a single conductive pattern and multiple sweeping contacts, the encoder 1100 can include multiple channels in the conductive pattern 1120 in fixed alignment mounted on a substrate and a single sweeping contact that sweeps across the multiple channels of the pattern.

Robust Communication

Insulin is a lifesaving drug for people with diabetes, but an overdose can be dangerous or even lethal. For this reason, it is critical for the system to keep an accurate record of all insulin taken by the patient. If the user is relying on the system (for example, an app display) to recommend doses or remind them that they have not yet taken a dose, any interruption in the performance of the device or its communication with the display could lead to the system missing actual doses taken. For instance, the user may have taken a dose, but if the system does not receive this as input or identify a fault condition, it could over-recommend the next dose and possibly lead to overdose. Other drugs, besides insulin, taken with a smart delivery system may have similar dangers if over-dosed.

To improve safety and guarantee the user that data is current and correct, it is helpful to have fail-safes for the following scenarios. For example, the example encoders detect fault conditions, as described above for the various embodiments, when: (i) the pen's sensor becomes disconnected or damaged; (ii) the pen's sensor is shorted due to damage or flooding with liquid; and/or (iii) the pen's sensor wears out and signal becomes unreliable. For example, the example fault conditions can be detected by the system due to transmission and reception faults, when: (i) the pen's electronics or software malfunction such that it stops transmitting; and/or there is a transmission issue between the pen and app, e.g., such as interference, poor reception, or the companion device 5 being in a non-communication mode (e.g., airplane mode on a smartphone).

To robustly identify transmission and reception fault conditions, the display (e.g., the app resident on the companion device 5) must ensure that the medicine dispensing device is operational, communication is functioning correctly, and data is up to date.

One example method for accomplishing this include the following. The pen device 10 may periodically (e.g., every 2 seconds) transmit a beacon indicating that its self-tests are successful, even if there is no new data to transmit. In this way, if the beacon is not received, regardless of the cause, the app can identify that there is a system fault and the potential for dose information to be incomplete.

Another example method to ensure the pen device 10 is operational, communicating correctly and up-to-date with data includes the following: the app may send a request to the pen device 10 to transmit status. The pen device 10 would then respond with its status, validating that the system is functioning. If a response is not received, then this indicates a system fault.

In some implementations, the beacon or response from the device may also incorporate encryption or a walking code to protect against malicious interference from an attacker, further ensuring that the user's own pen is connected.

In some implementations, the beacon from the device may be initiated by a user action such as a button press or dialing a dose. For example, the app may prompt the user to press a button on the pen to transmit its status and indicate that the system is functioning properly.

Example embodiments of a medicine delivery system are described which includes a device with a fault-identifying encoder, and an app that monitors for proper communication with the device and displays appropriate messages if communication is lost for any reason. With end-to-end fault detection, a patient user of the system can be sure that the displayed dosing information is accurate, and if there is a fault anywhere in the system that could lead to an actual dose being missed, it will be communicated.

EXAMPLES

In some embodiments in accordance with the present technology (example 1), a system for administering a medicine to a patient includes an injection pen device, the injection pen device structured to contain a medicine cartridge and include: a dose setting mechanism to set a dose of a medicine stored in the medicine cartridge to be dispensed by the injection pen device, a dispensing mechanism to dispense the medicine according to the set dose, a sensor unit to detect a dispensed dose, an electronics unit including a processor, a memory, and a wireless transmitter, the electronics unit configured to process the detected dispensed dose with time data associated with a dispensing event to generate dose data, and to wirelessly transmit the dose data, and a multi-channel encoder, in communication with the electronics unit and one or both of the dose setting mechanism and the dispensing mechanism, to monitor a dose setting operation and/or a dose dispensing operation; and the injection pen device is capable of being in wireless communication with a mobile communication device that includes a data processing unit including a processor and memory to receive and process the dose data, wherein one or both of the electronics unit of the injection pen device or the data processing unit of the mobile communication device are configured to determine a fault based on a detected error and/or a quality of signal from the multi-channel encoder.

Example 2 includes the system of example 1, wherein the multi-channel encoder includes: a first component including a substrate and a pattern of electrically conductive segmented contact pads in a first region of the substrate, and a plurality of channel pads disposed on the substrate in a second region, the plurality of channel pads including an electrical ground pad and at least three input channel pads, wherein the at least three input channel pads include a first channel and a second channel associated with measuring rotation of the dose setting mechanism and/or the dispensing mechanism, and a third channel associated with holding at least some of the pattern of segmented contact pads at electrical ground during a sweep of the pattern; and a second component including an electrically conductive sweeping contact that electrically interfaces with individual segmented contact pads of the first component, one at a time, during the sweep of the pattern, wherein the second component is configured to rotate about a shared axis with the first component, or vice versa, such that the sweeping contact sweeps along the pattern of segmented contact pads during rotation.

Example 3 includes the system of example 2, wherein the first component and the second component are configured as annular rings.

Example 4 includes the system of example 2, wherein the first component includes a printed circuit board, and the pattern of segmented contact pads and the plurality of channel pads include planar metallic contacts.

Example 5 includes the system of example 2, wherein the sweeping contact includes a spring-loaded arm that is coupled to a body of the second component.

Example 6 includes the system of example 2, wherein the first component further includes one or more base pads electrically coupled to the electrical ground pad.

Example 7 includes the system of example 6, wherein the multi-channel encoder further includes one or more spring connectors to interface between the second component and the one or more base pads, wherein the second component includes an interior track along a side of the second component that faces the first component such that second component slides along a contacting surface of the spring connectors in the interior track as the sweeping contact sweeps across the pattern of segmented contact pads during rotation.

Example 8 includes the system of example 2, wherein the third channel of the multi-channel encoder is operable to actively monitor ground for detection of damage to the injection pen device.

Example 9 includes the system of example 1, wherein the fault is determined based on signal quality analysis of one or more of electrical noise, signal frequency error, phase error, duty cycle error.

Example 10 includes the system of example 1, wherein the fault is determined based on monitoring of channel disconnection or channel short circuit associated with the multi-channel encoder.

Example 11 includes the system of example 1, wherein the determined fault is based on a contaminant or a water ingress in the injection pen device.

Example 12 includes the system of example 11, wherein the third line the contaminant or the water ingress in the multi-channel encoder bridges an active signal monitoring channel and a channel connected to ground to cause a detectable voltage drop indicative of the fault with the injection pen device.

Example 13 includes the system of example 1, wherein the injection pen device is operable to transmit a beacon to the companion device periodically indicative of normal function of the injection pen device, such that the data processing unit of the companion device is configured to (i) detect the fault when the beacon is not received within one or more of the beacon periods and (ii) produce an alert to be presented on the companion device indicative of the fault and/or (iii) disable a module associated with display or calculation of the medicine.

Example 14 includes the system of example 1, wherein at least one of the injection pen device or the mobile communication device includes a software application program product comprising a non-transitory computer-readable storage medium having instructions, which when executed by the processor, cause the device to process the output signal data from the recorder to detect a fault in one or both of the dose setting mechanism and the dispensing mechanism of the injection pen device, and to generate an alert associated with the detected fault.

Example 15 includes the system of example 14, wherein the instructions of the software application program product, which when executed by the processor, further cause the device to process communication data between the injection pen device and the mobile communications device to determine a loss of communications, and to generate an alert associated with the determined loss of communications.

Example 16 includes the system of example 1, wherein the mobile communication device is implemented on a smartphone, a tablet, a wearable computing device including a smartwatch or smartglasses, a computer including a laptop computer, or one or more computers networked in a communication network through the Internet.

In some embodiments in accordance with the present technology (example 17), multi-channel encoder for medicament injection device includes a first component including a substrate and a pattern of electrically conductive segmented contact pads in a first region of the substrate, and a plurality of channel pads disposed on the substrate in a second region, the plurality of channel pads including an electrical ground pad and at least three input channel pads, wherein the at least three input channel pads include a first channel and a second channel associated with measuring rotation of a dose setting and/or dispensing mechanism of the medicament injection pen, and a third channel associated with holding at least some of the pattern of segmented contact pads at electrical ground during a sweep of the pattern; and a second component including an electrically conductive sweeping contact that electrically interfaces with individual segmented contact pads of the first component, one at a time, during the sweep of the pattern, wherein the second component is configured to rotate about a shared axis with the first component, or vice versa, such that the sweeping contact sweeps along the pattern of segmented contact pads during rotation wherein the multi-channel encoder is in communication with a processing unit of the medicament injection pen.

Example 18 includes the multi-channel encoder of example 17, wherein the first component and the second component are configured as annular rings.

Example 19 includes the multi-channel encoder of example 17, wherein the first component includes a printed circuit board, and the pattern of segmented contact pads and the plurality of channel pads include planar metallic contacts.

Example 20 includes the multi-channel encoder of example 17, wherein the sweeping contact includes a spring-loaded arm that is coupled to a body of the second component.

Example 21 includes the multi-channel encoder of example 17, wherein the first component further includes one or more base pads electrically coupled to the electrical ground pad.

Example 22 includes the multi-channel encoder of example 21, wherein the multi-channel encoder further includes one or more spring connectors to interface between the second component and the one or more base pads, wherein the second component includes an interior track along a side of the second component that faces the first component such that second component slides along a contacting surface of the spring connectors in the interior track as the sweeping contact sweeps across the pattern of segmented contact pads during rotation.

Example 23 includes the multi-channel encoder of example 17, wherein the third channel of the multi-channel encoder is operable to actively monitor ground for detection of damage to the injection pen device.

In some embodiments in accordance with the present technology (example 24), a system for administering a medicine to a patient includes an injection pen device, wherein the injection pen device includes an electronics unit including a processor and a memory, and the injection pen device includes an encoder (e.g., rotary encoder) to monitor a dose setting operation and/or a dose dispensing operation, the encoder including a pattern of contact pads in which at least a portion of the contact pads include a resistive material, where the processor is configured to analyze an output signal of the encoder to determine a rotation of a dose setting and/or dose dispensing mechanism of the injection pen and/or to estimate an amount of a medicine (e.g., insulin) dispensed or pre-set for dispensing from the injection pen device. In some example embodiments, the system is configured to confirm that the output signal is within a threshold of an expected signal (e.g., voltage) based on an electrical resistance associated with the pattern of contact pads. In such example embodiments, the system is configured to determine a short circuit when an analyzed voltage output is above the threshold of the expected signal and identify a short circuit fault condition, and/or the system is configured to determine an open circuit when an analyzed voltage output is below the threshold of the expected signal and identify an open circuit fault condition, such that the identified fault conditions are indicative of one or more of a dirty or contaminated electrical contact or connection in the multi-channel encoder, a corroded or damaged electrical contact or connection within the multi-channel encoder, or an ingress of a liquid within the multi-channel encoder.

Implementations of the subject matter and the functional operations described in this disclosure can be implemented in various systems, digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible and non-transitory computer readable medium for execution by, or to control the operation of, data processing apparatus. The computer readable medium can be a machine-readable storage device, a machine-readable storage substrate, a memory device, a composition of matter effecting a machine-readable propagated signal, or a combination of one or more of them. The term "data processing unit" or "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of nonvolatile memory, media and memory devices, including by way of example semiconductor memory devices, e.g., EPROM, EEPROM, and flash memory devices. The processor and the memory can be supplemented by, or incorporated in, special purpose logic circuitry.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While this disclosure contains many specifics, these should not be construed as limitations on the scope of what may be claimed, but rather as descriptions of features that may be specific to particular embodiments of this disclosure. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this disclosure should not be understood as requiring such separation in all embodiments.

Only a few implementations and examples are described, and other implementations, enhancements, and variations can be made based on what is described and illustrated in this disclosure.

What is claimed is:

1. A multi-channel pattern encoder for an insulin injection device, comprising:
   a processing unit;
   a voltage source electrically coupled to an input of the processing unit via a pull-up resistor configured to pull the input of the processing unit to a high logic signal;
   a conductive pattern having a plurality of contact pads electrically coupled to ground; and
   an electrically conductive sweeping contact electrically coupled to the input of the processing unit and to the voltage source via the pull-up resistor, the sweeping contact configured to rotate relative to the conductive pattern about a shared axis to move into contact and out of contact with the conductive pattern, wherein:
   the sweeping contact is electrically grounded when the sweeping contact is contacting at least one contact pad of the plurality of contact pads such that current flows from the voltage source to ground through the pull-up resistor and no voltage is detected at the input of the processing unit; and
   a voltage is detected at the input of the processing unit when the sweeping contact is not contacting at least one contact pad of the plurality of contact pads such that there is no current flow from the voltage source to ground through the pull-up resistor.

2. The multi-channel pattern encoder according to claim 1, wherein the voltage source is a +2V voltage source.

3. The multi-channel pattern encoder according to claim 2, wherein the voltage detected at the input of the processing unit is 2V.

4. The multi-channel pattern encoder according to claim 1, wherein the sweeping contact is spring-loaded.

5. The multi-channel pattern encoder according to claim 1, wherein the sweeping contact and the conductive pattern are coupled to each other by at least one electrically conductive spring extending therebetween.

6. The multi-channel pattern encoder according to claim 1, wherein the sweeping contact and the conductive pattern are annular rings surrounding the shared axis.

7. The multi-channel pattern encoder according to claim 1, wherein the sweeping contact is configured to contact more than one contact pad at a time.

8. A multi-channel pattern encoder for an insulin injection device, comprising:
   a processing unit;
   a pull-up resistor electrically coupled to an output of the processing unit and configured to pull the output of the processing unit to a high logic signal;
   a conductive pattern having a plurality of contact pads electrically coupled to ground; and
   an electrically conductive sweeping contact electrically coupled to an input of the processing unit and to the output of the processing unit via the pull-up resistor, the sweeping contact configured to rotate relative to the conductive pattern about a shared axis to move into contact and out of contact with the conductive pattern, wherein:
      the sweeping contact is electrically grounded when the sweeping contact is contacting at least one contact pad of the plurality of contact pads such that current flows from the output of the processing unit to ground through the pull-up resistor and no voltage is detected at the input of the processing unit, and
      a voltage is detected at the input of the processing unit when the sweeping contact is not contacting one of the plurality of contact pads such that there is no current flow from the output of the processing unit to ground through the pull-up resistor.

9. The multi-channel pattern encoder according to claim 8, wherein the output of the processing unit is a switchable output set to a positive voltage to enable an encoder channel of the multi-channel pattern encoder.

10. The multi-channel pattern encoder according to claim 9, wherein the positive voltage is +2V.

11. The multi-channel pattern encoder according to claim 8, wherein the output of the processing unit is configured to be disabled such that there is no current flow from the output of the processing unit to ground through the pull-up resistor when the sweeping contact is contacting at least one contact pad of the plurality of contact pads.

12. The multi-channel pattern encoder according to claim 8, wherein the sweeping contact is spring-loaded.

13. The multi-channel pattern encoder according to claim 8, wherein the sweeping contact and the conductive pattern are coupled to each other by at least one electrically conductive spring extending therebetween.

14. The multi-channel pattern encoder according to claim 8, wherein the sweeping contact and the conductive pattern are annular rings surrounding the shared axis.

15. The multi-channel pattern encoder according to claim 8, wherein the sweeping contact is configured to contact more than one contact pad at a time.

16. A multi-channel pattern encoder for an insulin injection device, comprising:
   a processing unit;
   a voltage source electrically coupled to an input of the processing unit via a pull-up resistor configured to pull the input of the processing unit to a high logic signal;
   a conductive pattern having a plurality of contact pads electrically coupled to the input of the processing unit and to the voltage source via the pull-up resistor; and
   an electrically conductive sweeping contact electrically coupled to ground, the sweeping contact configured to rotate relative to the conductive pattern about a shared axis to move into contact and out of contact with the conductive pattern, wherein:
      the conductive pattern is electrically grounded when the sweeping contact is contacting at least one contact pad of the plurality of contact pads such that current flows from the voltage source to ground through the pull-up resistor and no voltage is detected at the input of the processing unit; and
      a voltage is detected at the input of the processing unit when the sweeping contact is not contacting one of the plurality of contact pads such that there is no current flow from the voltage source to ground through the pull-up resistor.

17. The multi-channel pattern encoder according to claim 16, wherein the sweeping contact is spring-loaded.

18. The multi-channel pattern encoder according to claim 16, wherein the sweeping contact and the conductive pattern are coupled to each other by at least one electrically conductive spring extending therebetween.

19. The multi-channel pattern encoder according to claim 16, wherein the sweeping contact and the conductive pattern are annular rings surrounding the shared axis.

20. The multi-channel pattern encoder according to claim 14, wherein the voltage source is a +2V voltage source.

* * * * *